(12) United States Patent
Yamanaka et al.

(10) Patent No.: US 11,259,775 B2
(45) Date of Patent: Mar. 1, 2022

(54) ULTRASONIC WAVE TRANSMISSION AND RECEPTION DEVICE

(71) Applicant: HITACHI, LTD., Tokyo (JP)

(72) Inventors: Kazuhiro Yamanaka, Tokyo (JP); Kenichi Kawabata, Tokyo (JP); Takahide Terada, Tokyo (JP); Atsurou Suzuki, Tokyo (JP); Yushi Tsubota, Tokyo (JP); Wenjing Wu, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 569 days.

(21) Appl. No.: 16/244,841

(22) Filed: Jan. 10, 2019

(65) Prior Publication Data
US 2019/0223833 A1   Jul. 25, 2019

(30) Foreign Application Priority Data

Jan. 19, 2018   (JP) .............................. JP2018-007637

(51) Int. Cl.
*A61B 8/14* (2006.01)
*A61B 8/06* (2006.01)
(Continued)

(52) U.S. Cl.
CPC ................ *A61B 8/145* (2013.01); *A61B 8/06* (2013.01); *A61B 8/0875* (2013.01);
(Continued)

(58) Field of Classification Search
CPC ..... A61B 8/145; A61B 8/4444; A61B 8/4281; A61B 8/4461; A61B 8/0875; A61B 8/06;
(Continued)

(56) References Cited

U.S. PATENT DOCUMENTS

| 4,984,575 A | * | 1/1991 | Uchiyama | .......... A61B 17/2255 600/439 |
| 2005/0277824 A1 | * | 12/2005 | Aubry | ................. G01S 7/52049 600/407 |

(Continued)

FOREIGN PATENT DOCUMENTS

| JP | 57-107146 A2 | 7/1982 |
| JP | 2002-238898 A | 8/2002 |
| JP | 2016-120114 A | 7/2016 |

OTHER PUBLICATIONS

Japanese Office Action dated Apr. 27, 2021 for Japanese Patent Application No. 2018-007637.

*Primary Examiner* — Bo Joseph Peng
(74) *Attorney, Agent, or Firm* — Volpe Koenig

(57) ABSTRACT

Provided is a device that transmits and receives an ultrasonic wave to and from an entire periphery of a specimen while preventing a movement of the specimen. An ultrasonic wave transmission and reception device includes: an oscillator array that is arrayed with an oscillator, the oscillator transmitting and receiving an ultrasonic wave; a fixing tool that is disposed between the oscillator array and the specimen and retains the specimen; and a drive mechanism that presses at least a part of the fixing tool against the specimen as to retain the specimen. An ultrasonic wave transmitted by the oscillator array passes through the fixing tool and irradiates on the specimen, and as for the oscillator array, the oscillator array and the fixing tool are disposed in a positional relationship such that the ultrasonic wave reflected by and/or passing through by the specimen and passing through the fixing tool is received.

16 Claims, 16 Drawing Sheets

(51) Int. Cl.
   *A61B 8/00*       (2006.01)
   *G06T 7/00*       (2017.01)
   *G01S 15/89*      (2006.01)
   *A61B 8/08*       (2006.01)
   *A61B 8/13*       (2006.01)

(52) U.S. Cl.
   CPC .............. *A61B 8/4281* (2013.01); *A61B 8/44* (2013.01); *A61B 8/4444* (2013.01); *A61B 8/4461* (2013.01); *G01S 15/8906* (2013.01); *G06T 7/0012* (2013.01); *A61B 8/13* (2013.01); *A61B 8/4494* (2013.01); *G06T 2207/10132* (2013.01); *G06T 2207/30104* (2013.01)

(58) Field of Classification Search
   CPC ........... A61B 8/44; A61B 8/4494; A61B 8/13; G06T 7/0012; G06T 2207/30104; G06T 2207/10132; G01S 15/8906; G01S 7/52079; G01S 15/8929; G01S 15/8922
   See application file for complete search history.

(56) References Cited

U.S. PATENT DOCUMENTS

2006/0287596 A1\* 12/2006 Johnson ................... A61B 8/14
                                                          600/437
   2012/0029358 A1\*  2/2012 Lin ........................ A61B 8/406
                                                          600/447
   2017/0224305 A1\*  8/2017 Ho ........................ A61B 8/0825

\* cited by examiner

[FIG. 1]
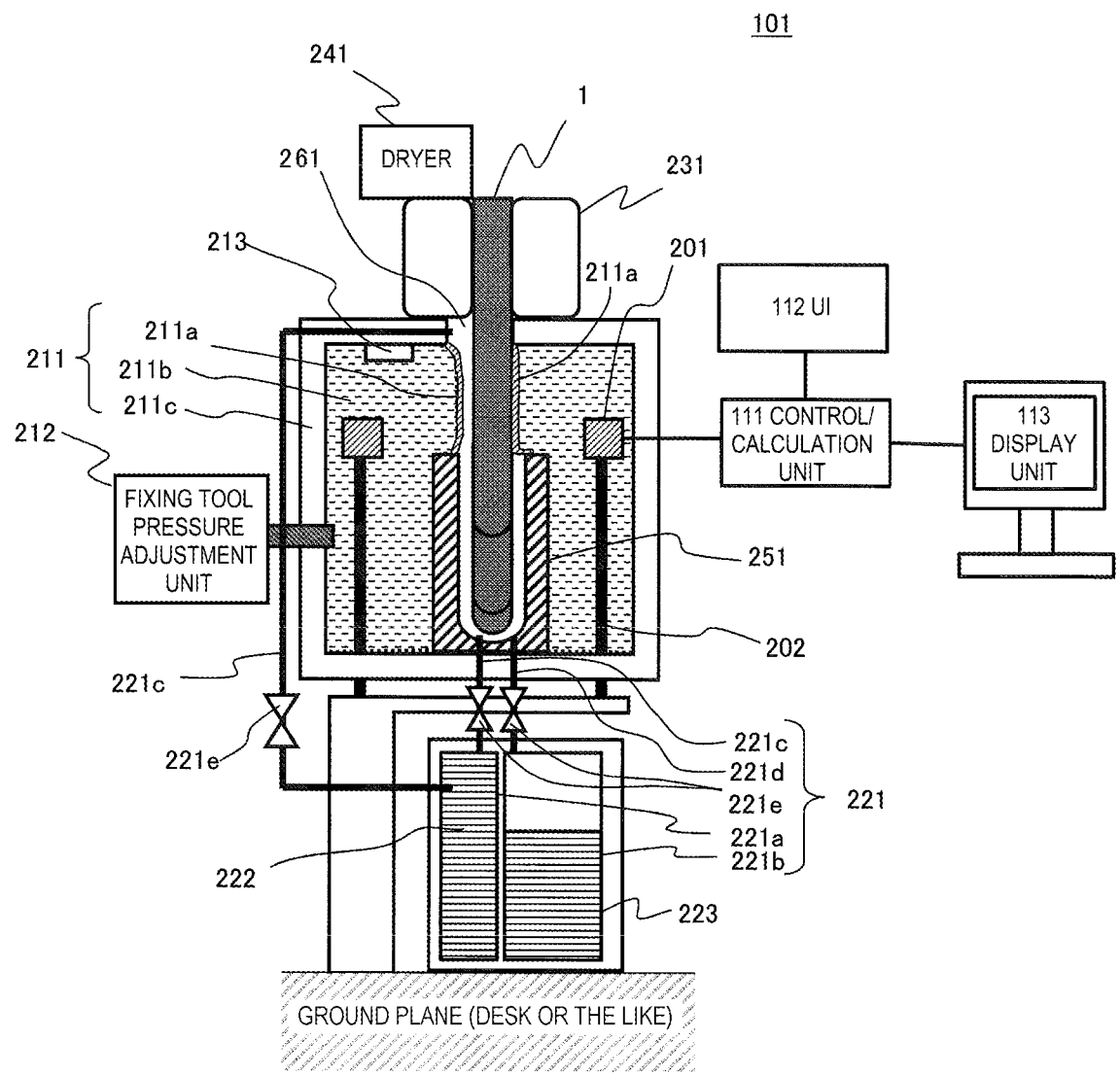

[FIG. 2]
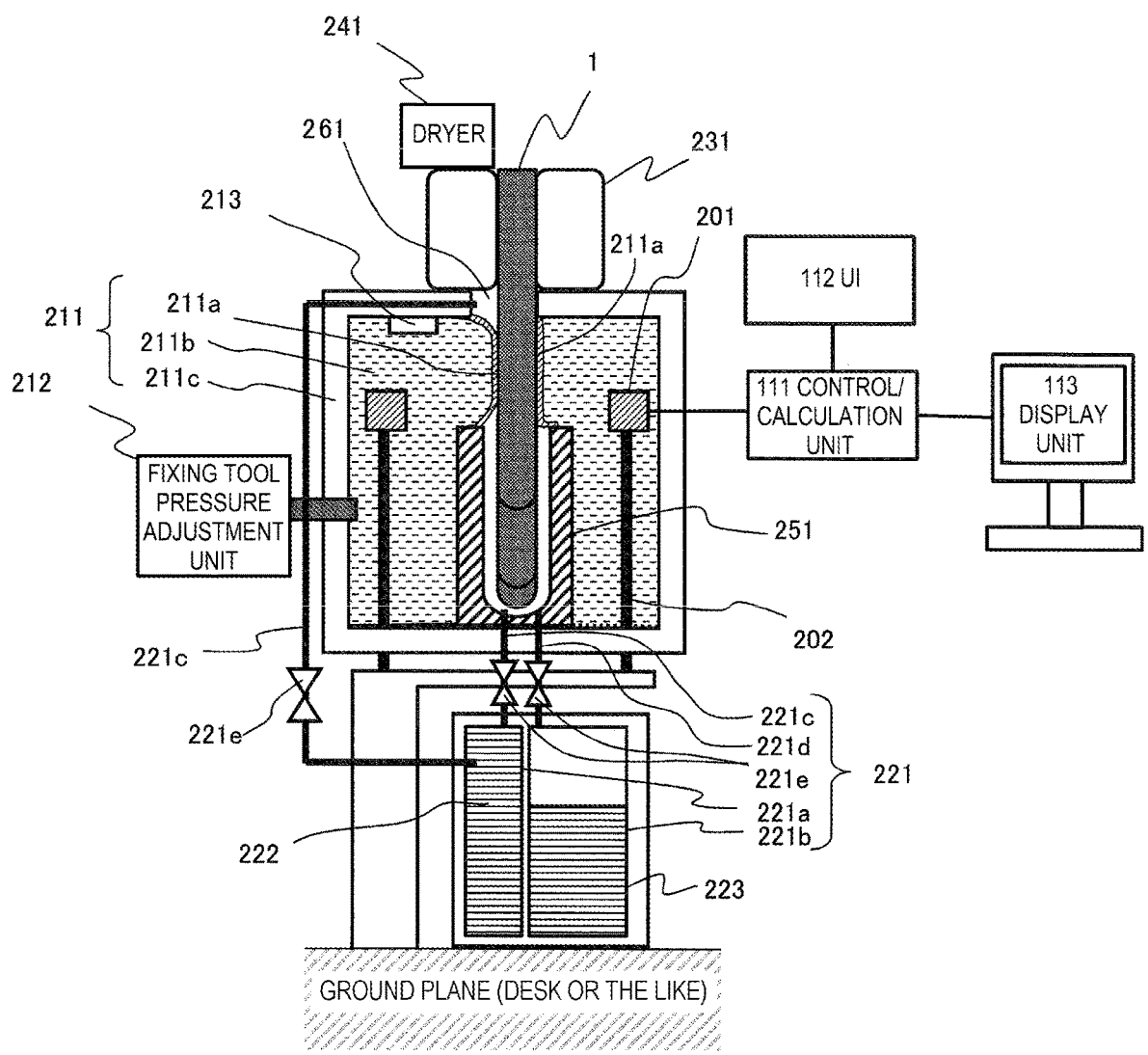

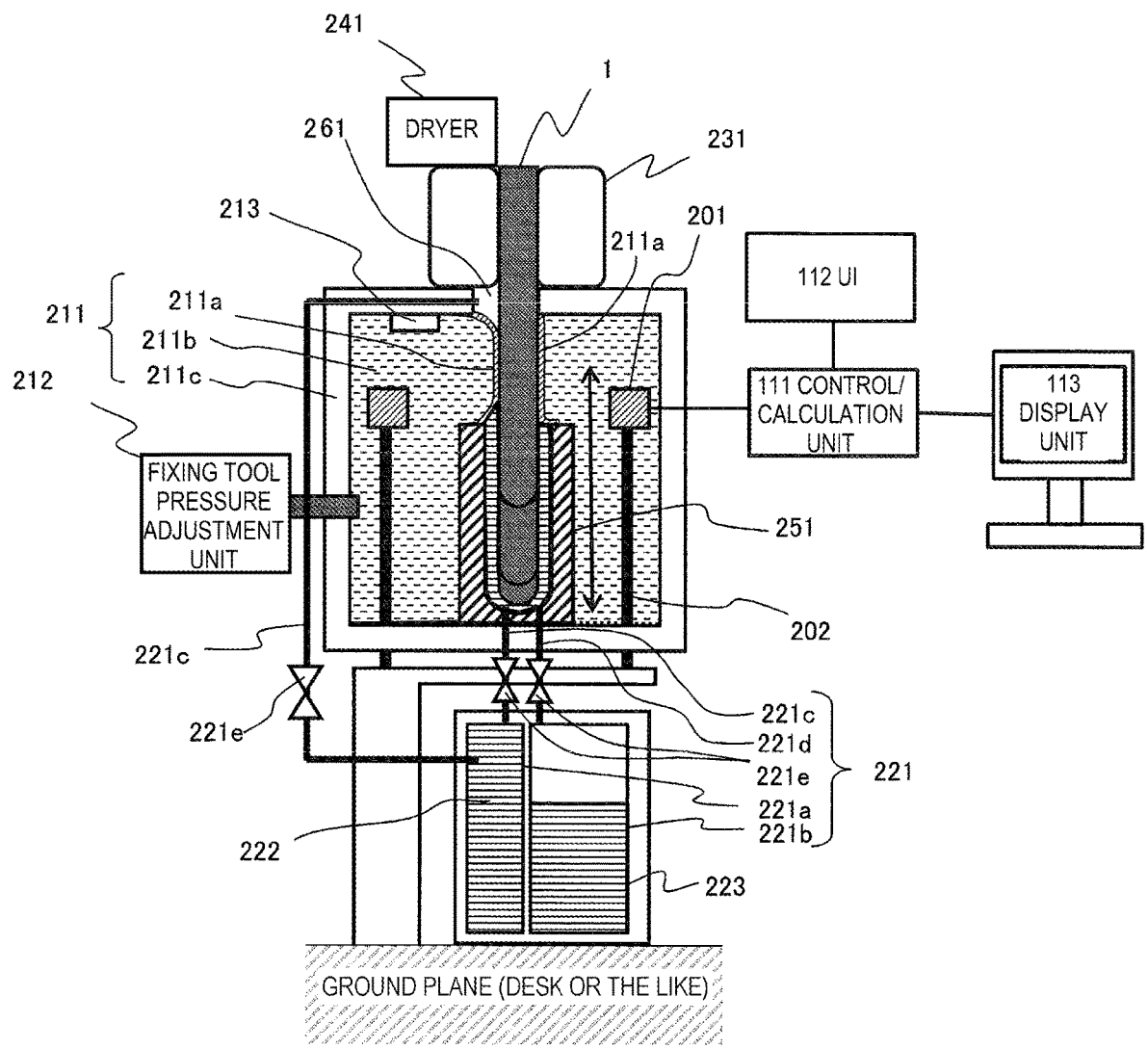
[FIG. 3]

[FIG. 4]
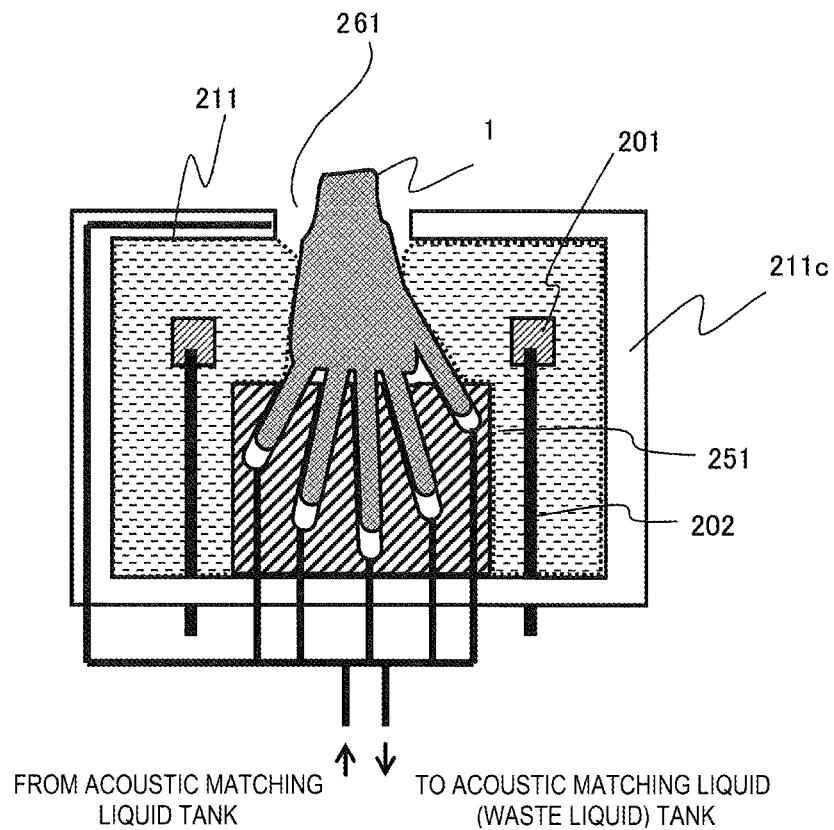
FROM ACOUSTIC MATCHING LIQUID TANK    TO ACOUSTIC MATCHING LIQUID (WASTE LIQUID) TANK

[FIG. 5]
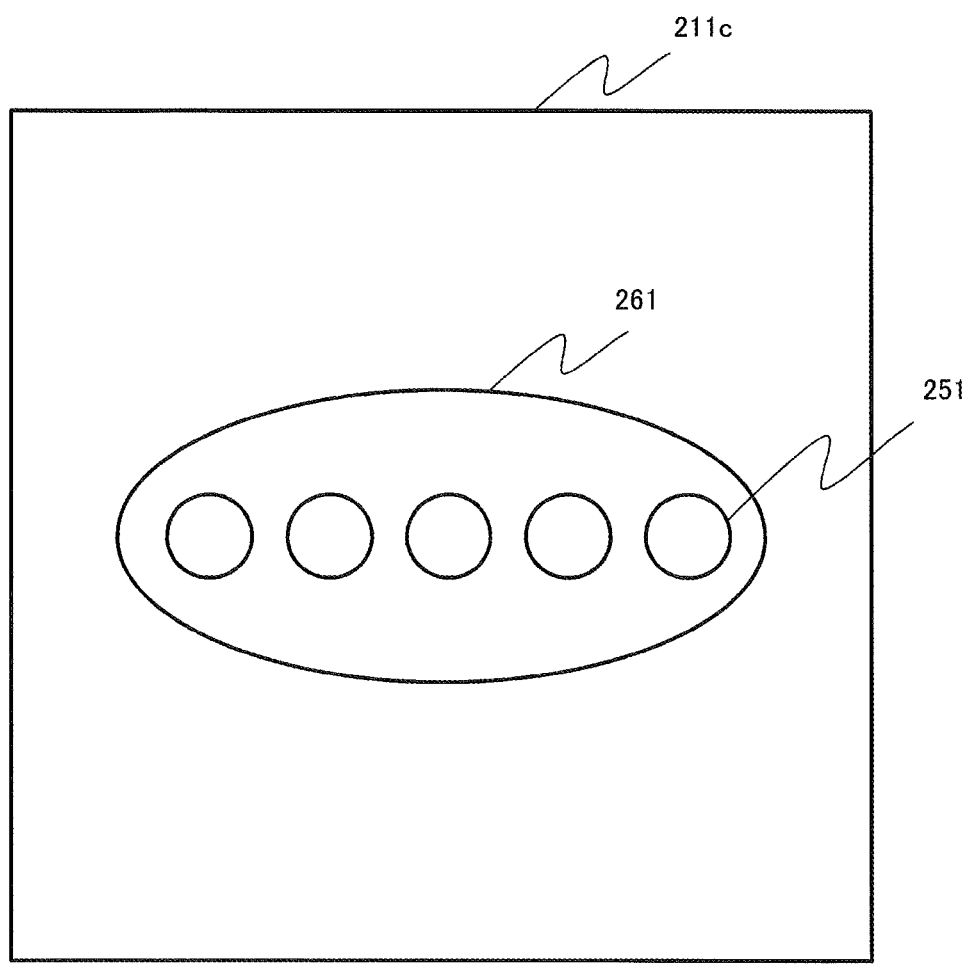

[FIG. 6A]
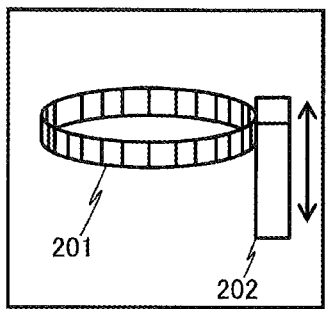
[FIG. 6B]
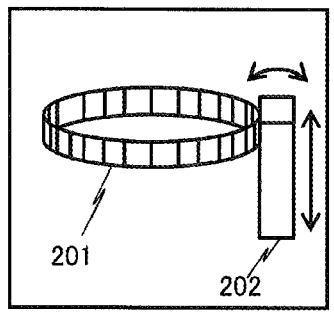
[FIG. 6C]
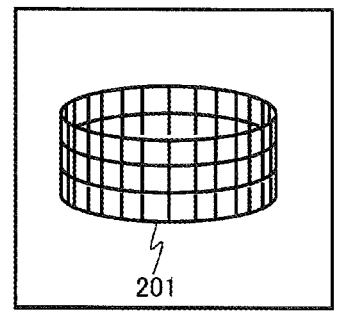
[FIG. 6D]
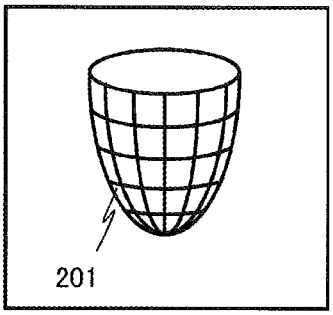
[FIG. 6E]
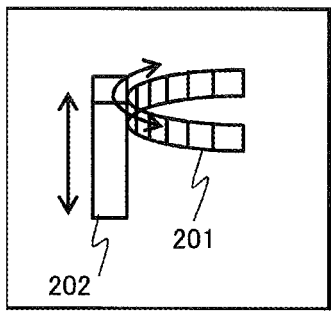
[FIG. 6F]
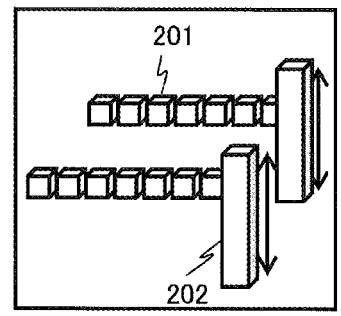

[FIG. 7]
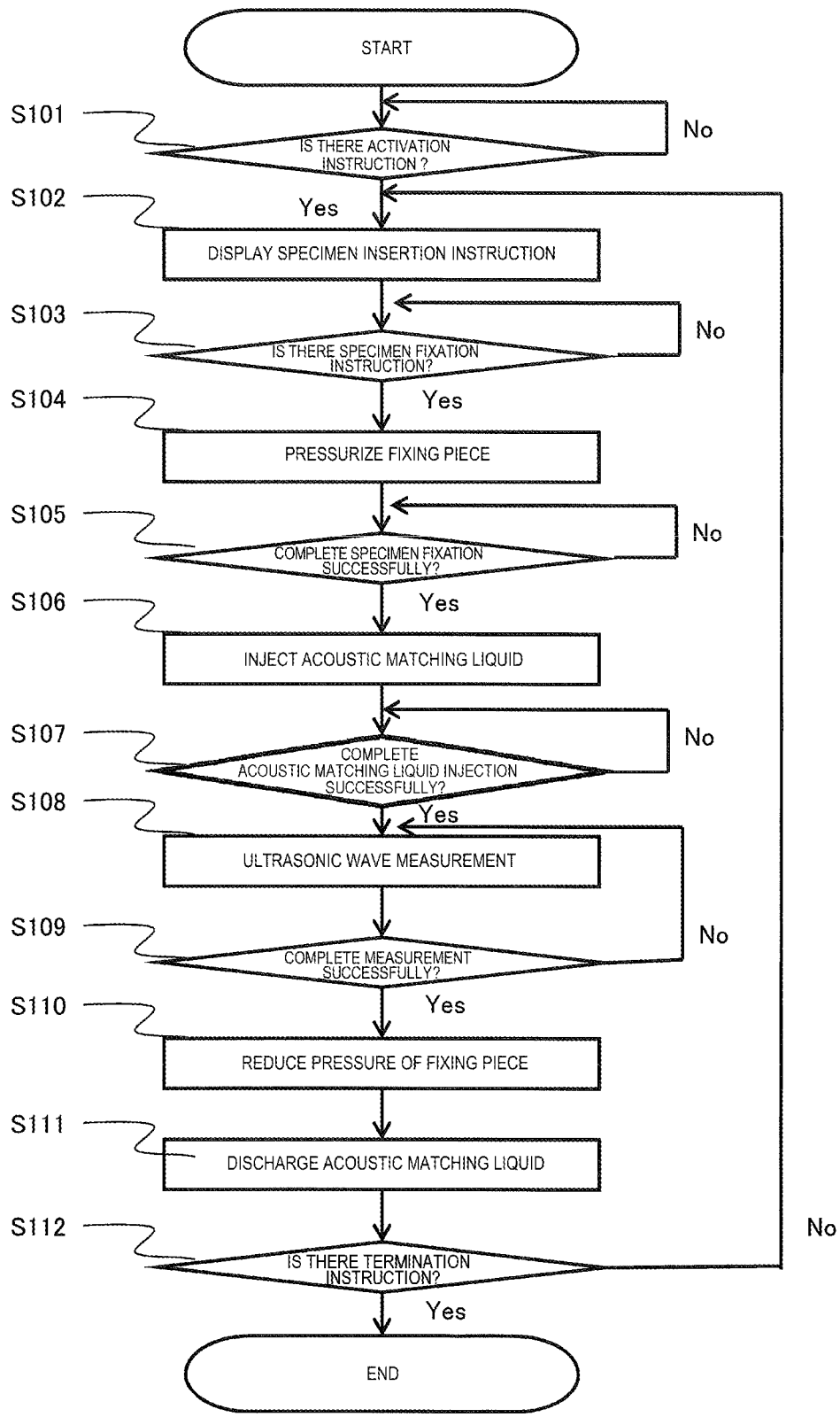

[FIG. 8]
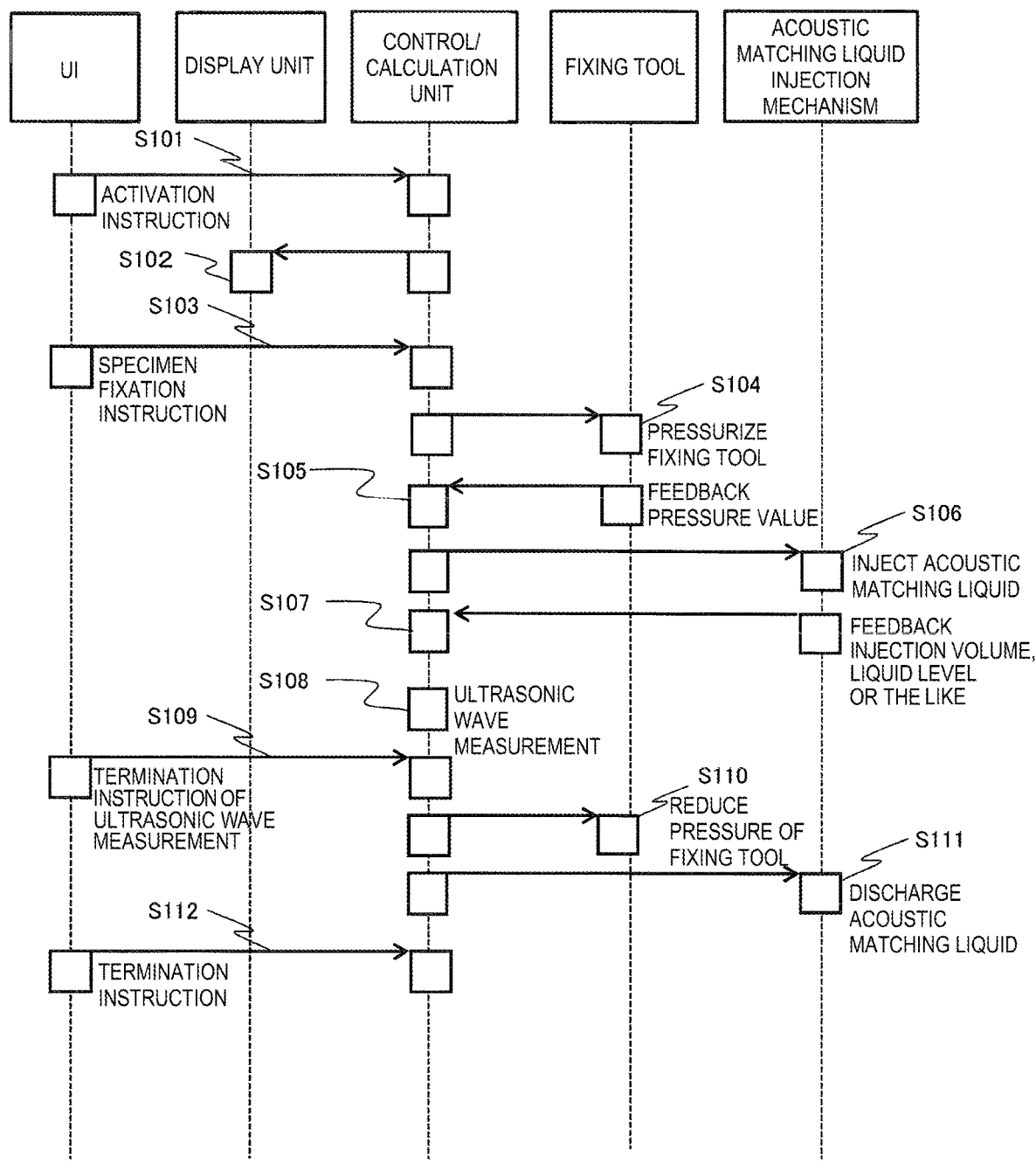

[FIG. 9]
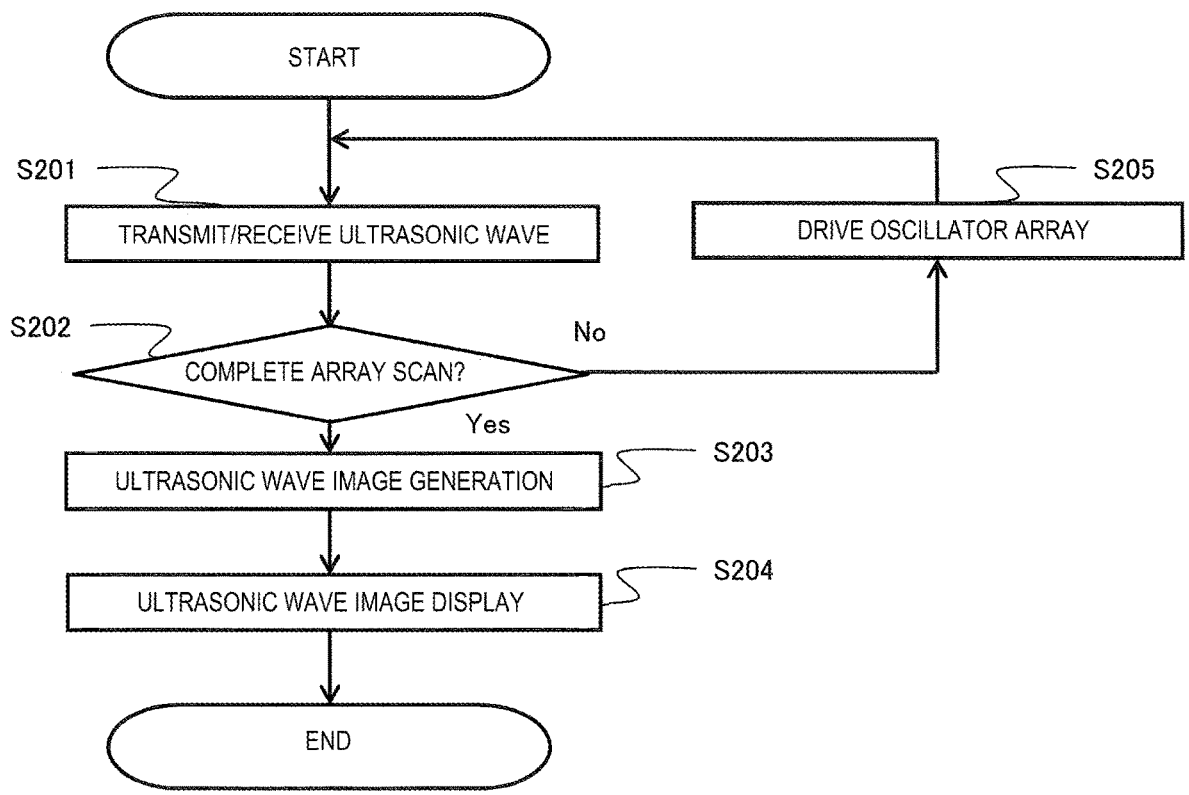

[FIG. 10]
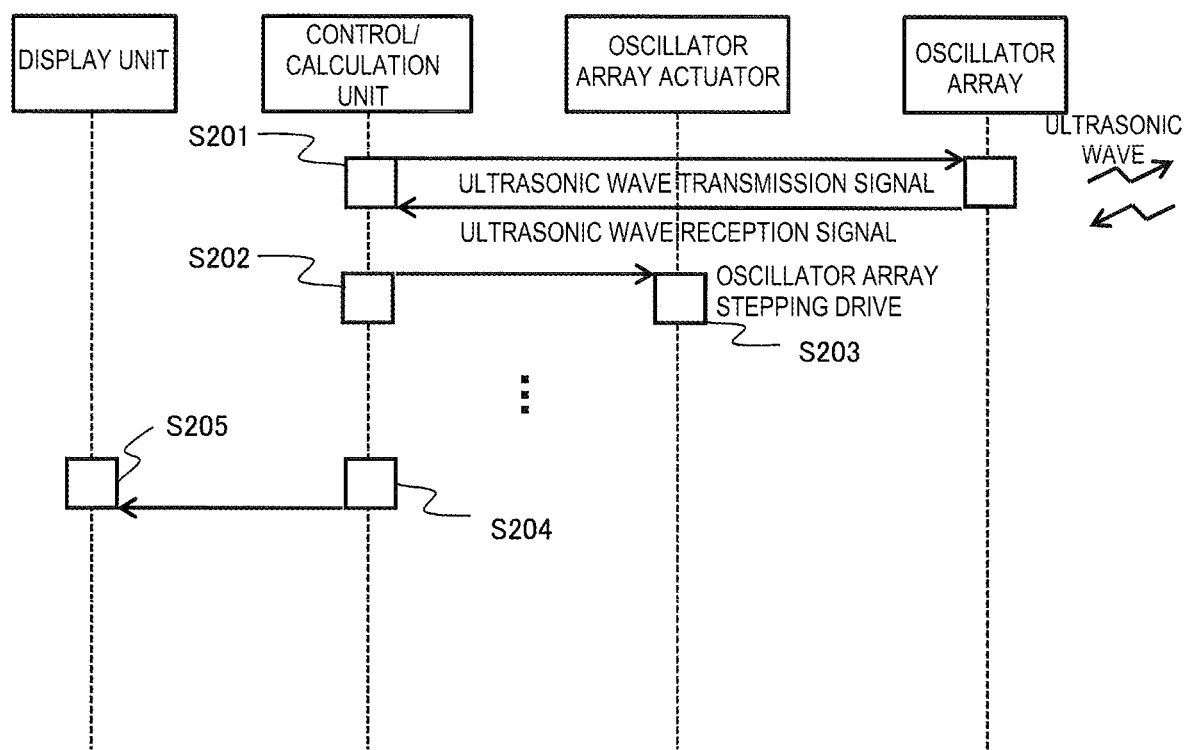

[FIG. 11]
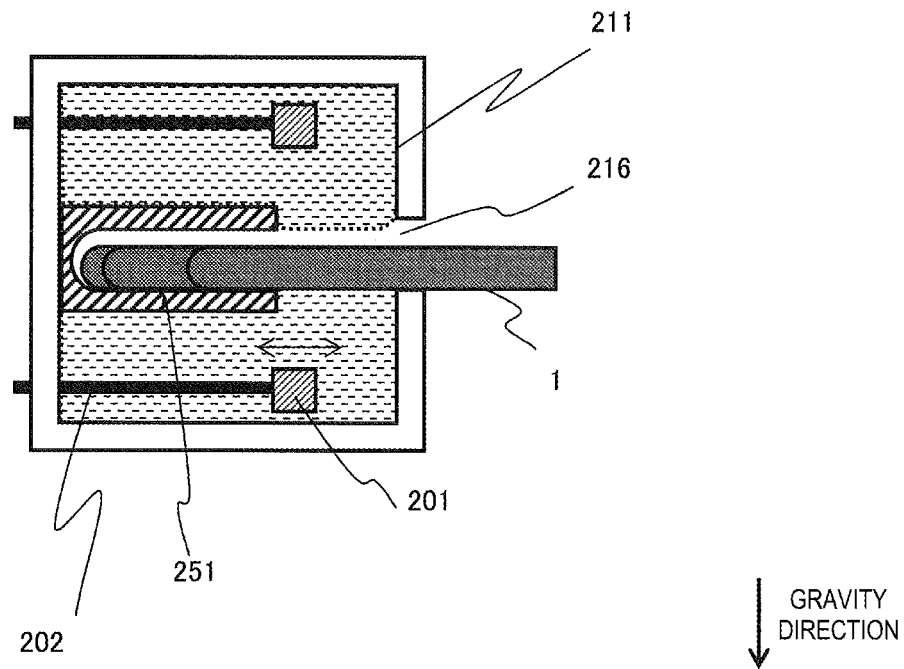
GRAVITY DIRECTION
[FIG. 12]
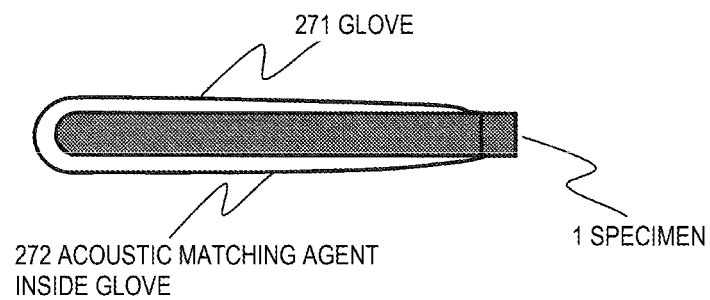

[FIG. 13]
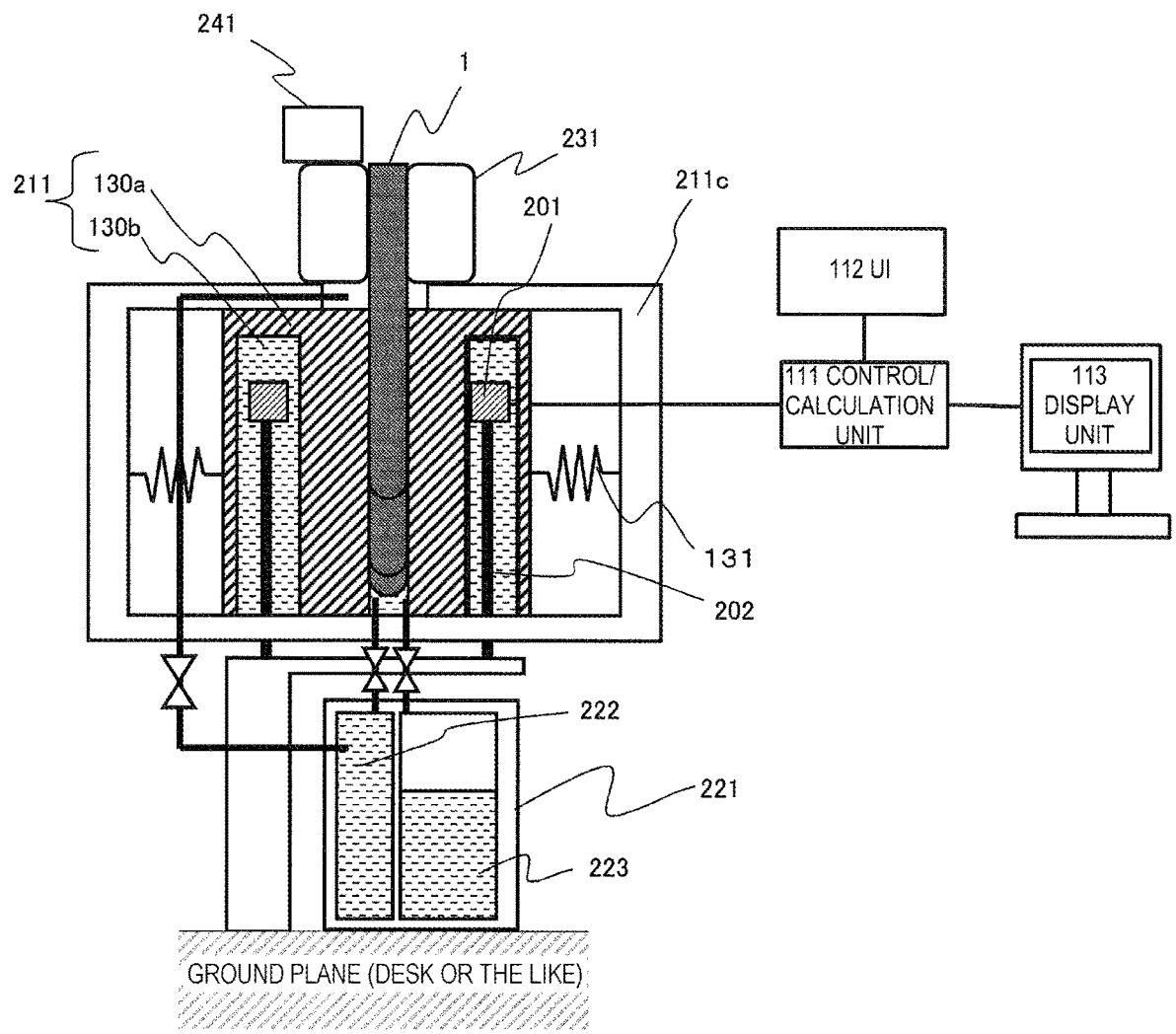

[FIG. 14]
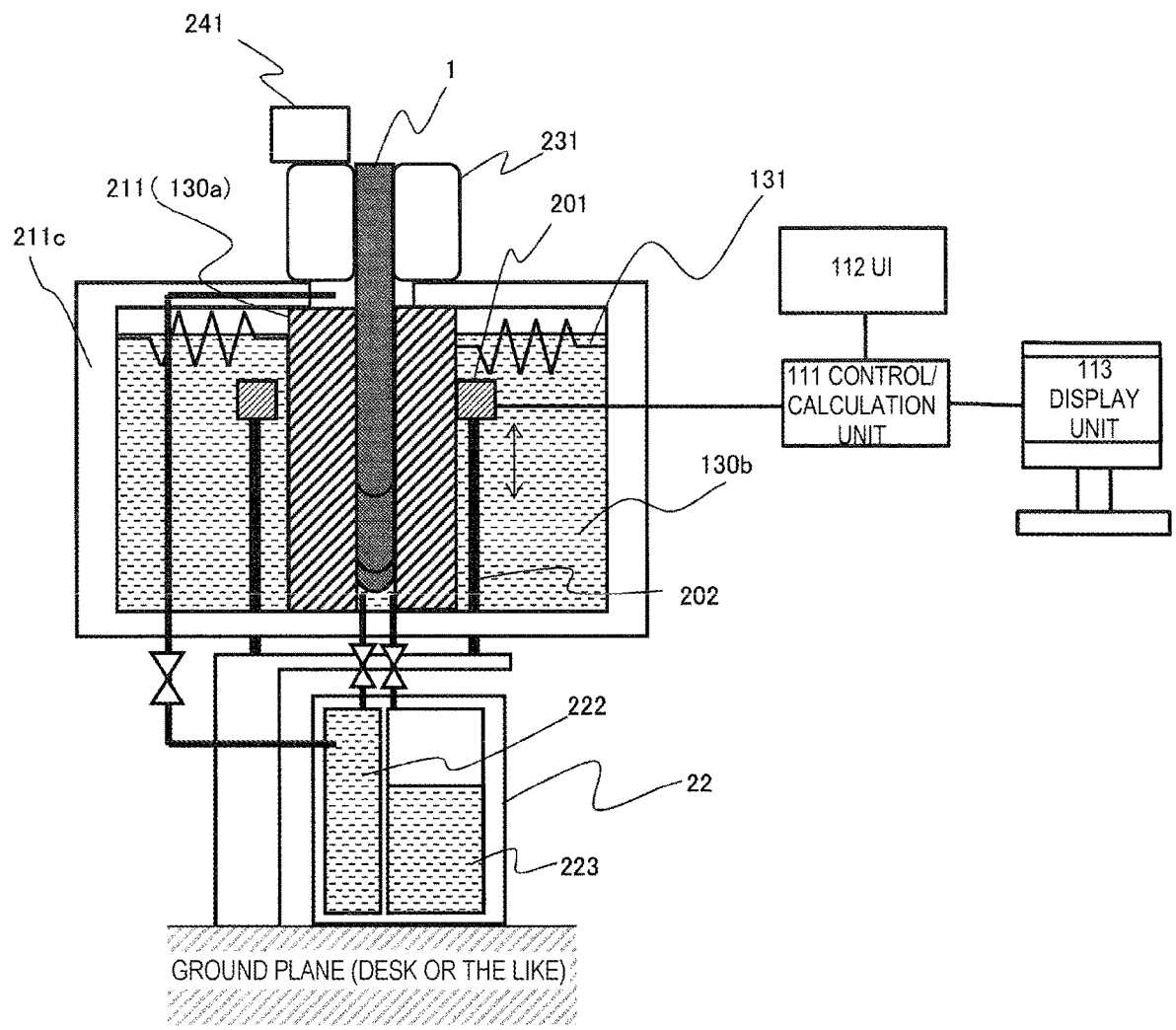

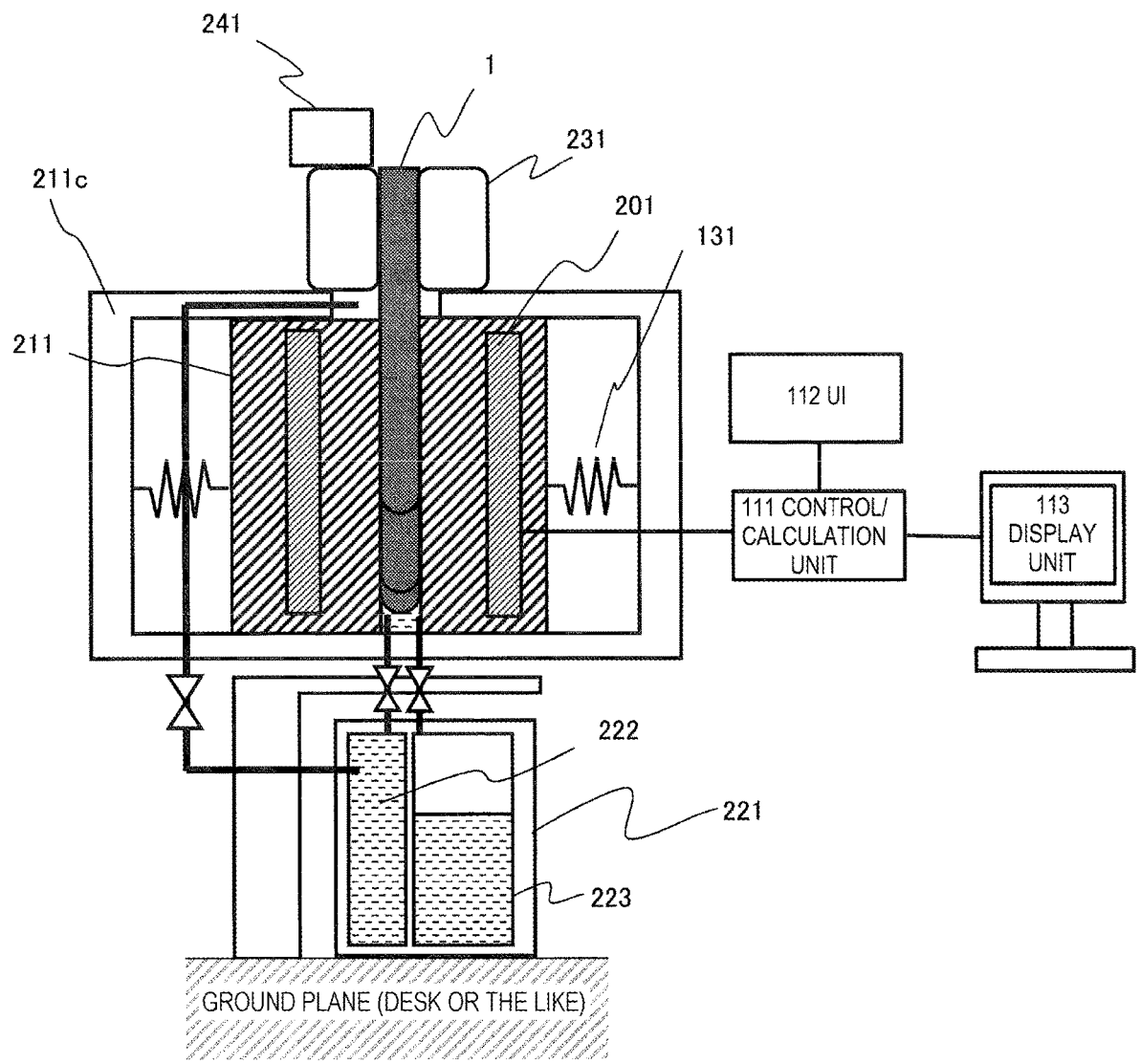
[FIG. 15]

[FIG. 16]
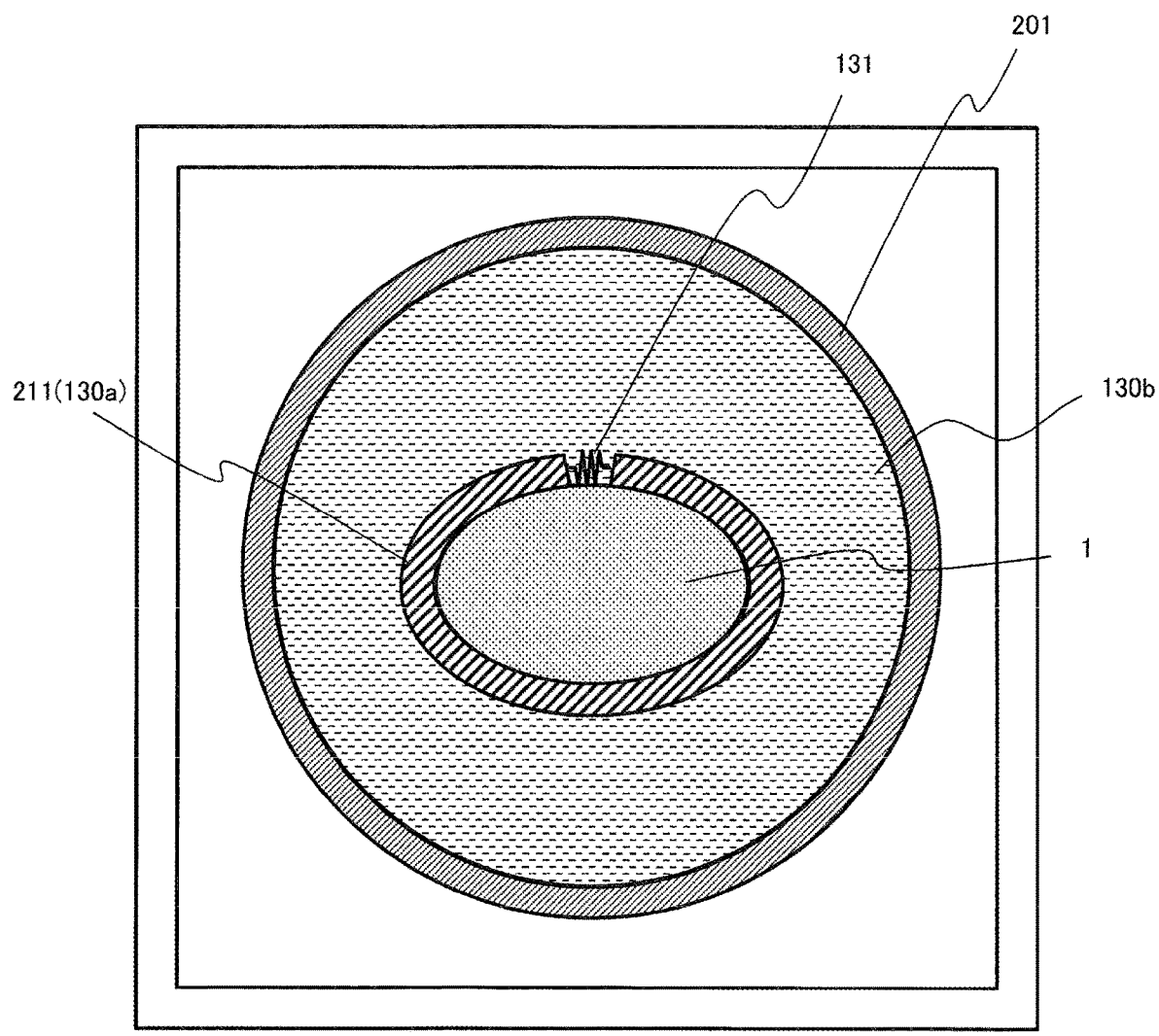

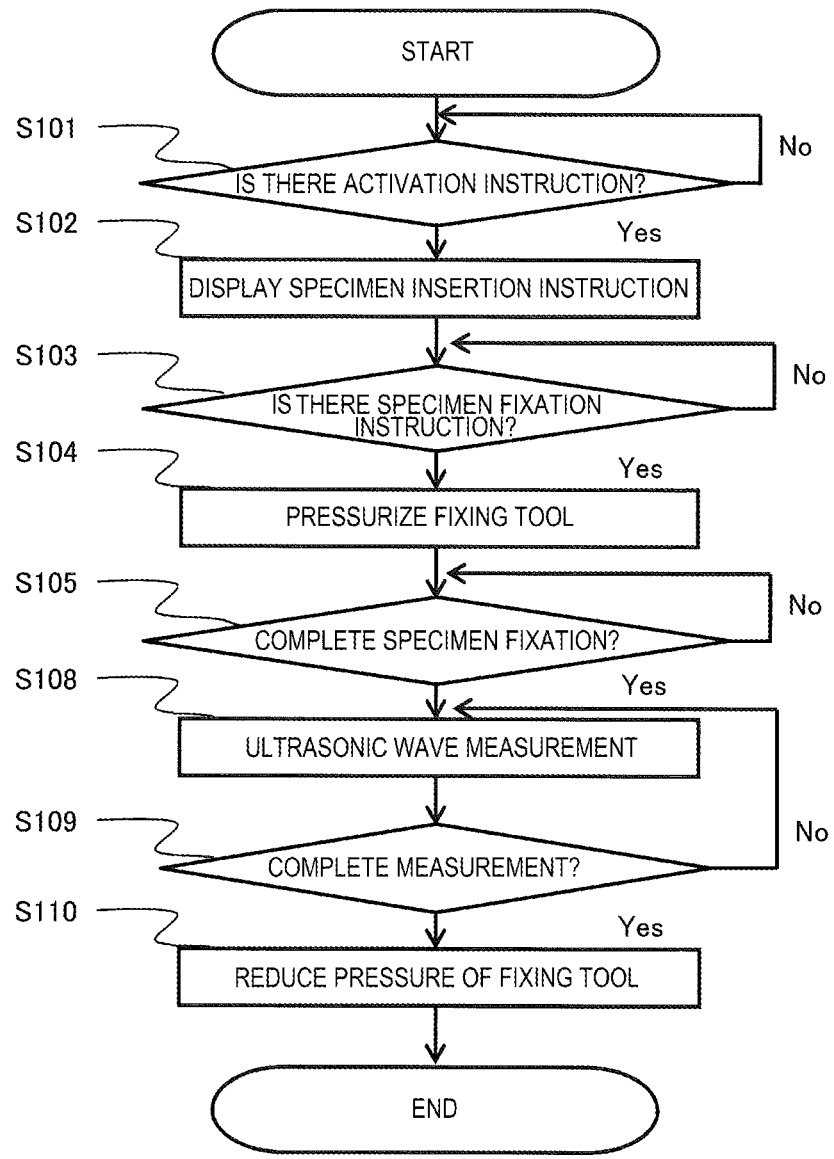

ULTRASONIC WAVE TRANSMISSION AND RECEPTION DEVICE

TECHNICAL FIELD

The present invention relates to an ultrasonic wave transmission and reception device, and particularly to a device that measures or images an object by using an ultrasonic wave signal.

BACKGROUND ART

The ultrasonic wave transmission and reception device is a device that transmits an ultrasonic wave to a specimen, receives an ultrasonic wave having a certain interaction with the specimen, measures certain information (for example, a blood flow velocity) relating to the specimen and images the specimen.

As an example, an ultrasonic wave echo device that receives a reflected ultrasonic wave from the specimen and generates an image of an inside of the specimen will be briefly described. In the ultrasonic wave echo device, an ultrasonic pulse is transmitted, and an echo signal reflected at a boundary between the specimen and an outside of the specimen, or at the inside of the specimen is received. An amplitude of a reception signal, which is recorded in a time axis direction, is called an A scan signal, the reception signal being output from each reception oscillator. The A scan signal is appropriately delayed or weighted according to a distance between the reception oscillator and a pixel or a voxel in an imaging region for each pixel or voxel within an imaging region set in the specimen and then is added (or averaged), and a reflection value is calculated. This processing is called a phasing processing. The reflection value subjected to a phasing processing is set as a luminance of a pixel corresponding to a position of each pixel or voxel, so that an echo image reflecting a structure of the specimen is generated. If necessary, an image processing such as an appropriate image filter is applied to the echo image. The echo image is displayed on a display screen.

A device using a photoacoustic method or an ultrasonic wave tomography method is taken as another example of the ultrasonic wave transmission and reception device. In the photoacoustic method, an ultrasonic wave generated by a local temperature rise is received, and imaged by the same method as the ultrasonic wave echo method, the local temperature rise being generated by irradiating high intensity light such as a pulsed laser to the specimen. Further, in the ultrasonic wave tomography method, an ultrasonic wave forward scattering (or passing through) in the specimen is received, and acoustic characteristics (such as a sound velocity and attenuation) of the specimen are calculated based on a propagation time, reception signal intensity, and a propagation distance of the ultrasonic wave, so that an acoustic characteristic map image is generated.

PTL 1 discloses a device that images a specimen by using the above photoacoustic method, and in order to prevent a movement of the specimen, a clip-shaped holder is attached to a side surface not opposing an acoustic receiver of the specimen.

PRIOR ART LITERATURE

Patent Literature

PTL 1: JP-A-2016-120114

SUMMARY OF INVENTION

Technical Problem

In recent years, in order to diagnose diseases causing deformation by inflammation in affected areas like rheumatism at an early stage, it is desired to have a highly accurate ultrasonic wave image such that minor changes caused by the inflammation before the deformation can be grasped. Therefore, it is necessary to accurately measure information (for example, blood flow information of a blood vessel) or the like that changes due to the disease by making the specimen stationary, and transmitting and receiving the ultrasonic wave to and from a periphery of the specimen.

Further, for an early diagnosis, it is desired to have a device that can automatically perform imaging by a technician or the specimen himself/herself with an easy operation, so that the device can be used for a medical examination, and it is desired to have a configuration that can make the specimen stationary with an easy operation.

Since the clip-shaped holder disclosed in PTL 1 is disposed on a side opposite to a side where an ultrasonic wave receiver is disposed, in a case where the ultrasonic wave is received only from one side of the specimen, the reception is not interfered. However, in order to obtain a highly accurate image of the specimen, it is desired to transmit and receive the ultrasonic wave to and from an entire periphery of the specimen, but influences of attenuation, reflection and refraction of the ultrasonic wave caused by the holder cannot be ignored. Therefore, the holder may be the reason of false image and deterioration in image quality.

Further, in the case of rheumatism, symptoms tend to appear at extremities (hands and feet) of limbs, and hands and feet are portions complicated in shapes and easy to move due to many joints. Thus, it is not easy to hold the clip while preventing a movement only with the clip as in PTL 1. Although it is possible to hold a large number of clips if the clips are attached to extremities of the specimen, a direction where the ultrasonic wave can be received may be limited. Furthermore, it is necessary to have a technician skilled at attaching the large number of clips to proper positions.

An object of the invention is to provide a device that can transmit and receive an ultrasonic wave to and from an entire periphery of a specimen while preventing a movement of the specimen with an easy operation.

Solution to Problem

To achieve the above object, the invention provides an ultrasonic wave transmission and reception device, including an oscillator array that is arrayed with an oscillator, the oscillator transmitting and receiving an ultrasonic wave; a fixing tool that is disposed between the oscillator array and a specimen and retains the specimen; and a drive mechanism that presses at least a part of the fixing tool against the specimen so as to retain the specimen. An ultrasonic wave transmitted by the oscillator array passes through the fixing tool and irradiates on the specimen, and as for the oscillator array, the oscillator array and the fixing tool are disposed in a positional relationship such that the ultrasonic wave reflected by and/or passing through the specimen and passing through the fixing tool is received.

Advantageous Effect

According to the invention, it is possible to provide a device that can transmit and receive an ultrasonic wave to and from an entire periphery of a specimen while preventing a movement of the specimen with an easy operation.

BRIEF DESCRIPTION OF DRAWINGS

FIG. 1 is a cross-sectional view showing an entire configuration of an ultrasonic wave transmission and reception device before a specimen is retained according to an Embodiment 1.

FIG. 2 is a cross-sectional view showing an entire configuration of the ultrasonic wave transmission and reception device after the specimen is retained according to the Embodiment 1.

FIG. 3 is a cross-sectional view showing an entire configuration of the ultrasonic wave transmission and reception device during ultrasonic wave measurement according to the Embodiment 1.

FIG. 4 is a cross-sectional view in a direction orthogonal to the cross-sectional views of FIGS. 1 to 3.

FIG. 5 is a top view of an ultrasonic wave imaging device.

FIGS. 6A to 6F are diagrams showing modifications an oscillator array and an actuator thereof in the ultrasonic wave transmission and reception device according to the Embodiment 1.

FIG. 7 is a flowchart showing an ultrasonic wave measurement operation of the ultrasonic wave transmission and reception device according to the Embodiment 1.

FIG. 8 is a sequence diagram showing information exchange between components of the ultrasonic wave transmission and reception device according to the Embodiment 1.

FIG. 9 is a flowchart showing an ultrasonic wave measurement operation of the ultrasonic wave transmission and reception device according to the Embodiment 1.

FIG. 10 is a sequence diagram showing information exchange between the components of the ultrasonic wave transmission and reception device according to the Embodiment 1.

FIG. 11 is a cross-sectional view showing a configuration of an ultrasonic wave transmission and reception device according to a Modification 1 of the Embodiment 1.

FIG. 12 is a view showing a cross section in a state where the specimen is inserted in a glove in a Modification 2 of the Embodiment 1.

FIG. 13 is a cross-sectional view showing a configuration of an ultrasonic wave transmission and reception device according to an Embodiment 2.

FIG. 14 is a cross-sectional view showing a configuration of an ultrasonic wave transmission and reception device according to a Modification 1 of the Embodiment 2.

FIG. 15 is a cross-sectional view showing a configuration of an ultrasonic wave transmission and reception device according to a Modification 2 of the Embodiment 2.

FIG. 16 is a cross-sectional view showing a configuration of an ultrasonic wave transmission and reception device according to a Modification 3 of the Embodiment 2.

FIG. 17 is a flowchart showing a simplified ultrasonic wave measurement operation of the ultrasonic wave transmission and reception device according to the Embodiment 2 and the Modifications 1 to 3 thereof.

DESCRIPTION OF EMBODIMENTS

An embodiment of the invention will be described with reference to the drawings.

Embodiment 1

An ultrasonic wave transmission and reception device 101 of the Embodiment 1 will be described with reference to FIGS. 1 to 5. FIGS. 1 to 3 are cross-sectional views showing an entire structure of the ultrasonic wave transmission and reception device, in which FIG. 1 shows a structure before a specimen is retained; FIG. 2 shows a structure after the specimen is retained; and FIG. 3 shows a structure during an ultrasonic wave measurement. FIG. 4 is a cross-sectional view in a direction orthogonal to the FIGS. 1 to 3. FIG. 5 is a top view of FIG. 1.

As shown in FIGS. 1 to 4, the ultrasonic wave transmission and reception device of the Embodiment 1 includes: an oscillator array 201 that is arrayed with an oscillator, the oscillator transmitting and receiving an ultrasonic wave; a fixing tool 211 that is disposed between the oscillator array 201 and a specimen 1 and retains the specimen 1; and a drive mechanism 212 that presses at least a part of the fixing tool 211 against the specimen 1 so as to retain the specimen 1. An ultrasonic wave transmitted by the oscillator array 201 passes through the fixing tool 211 and irradiates on the specimen 1, and as for the oscillator array 201, the oscillator array 201 and the fixing tool 211 are disposed in a positional relationship such that the ultrasonic wave reflected by and/or passing through the specimen 1 and passing through the fixing tool 211 is received.

Thus, in this embodiment, the oscillator array 201 has a configuration that transmits and receives the ultrasonic wave to and from the specimen 1 through the fixing tool 211. Thereby, the ultrasonic wave can be transmitted to and received from an entire periphery of the specimen because there is no limitation on disposition of the fixing portion 211. Further, since there is also no limitation on a shape of the fixing tool 211, it is possible to readily design the fixing tool 211 that can prevent a movement of the specimen with an easy operation.

In order to transmit and receive an ultrasonic wave through the fixing tool 211, it is desired that the fixing tool 211 is formed of a material having an acoustic impedance and/or sound velocity with respect to the ultrasonic wave transmitted by the oscillator array 201 equivalent to an acoustic impedance and/or a sound velocity of the specimen 1. Here, equivalent means that the impedance of the material constituting the fixing tool 211 is desirably from about 50% to 200% with respect to the impedance of the specimen 1, and the sound velocity of the material constituting the fixing tool 211 is desirably from about 50% to 200% with respect to the sound velocity of the specimen 1.

Further, it is desired that the oscillator array 201, as shown in shape examples in FIG. 6, have a shape that two-dimensionally surrounds at least a part of the periphery of the specimen 1. Accordingly, the reflected or passing wave of the specimen 1 can be obtained not only in one direction, but also from the entire periphery or a circumferential direction of a predetermined angular range, so that a highly accurate image of the specimen can be obtained. For example, as shown in FIGS. 6A to 6F, the oscillator array 201 can be arrayed to include at least one pair of oscillators disposed at opposing positions with the specimen 1 sandwiched therebetween.

An actuator 202 may be attached to the oscillator array 201 so as to move the oscillator array 201 relative to the specimen 1. Accordingly, the oscillator array 201 can move relative to the specimen 1, so that the specimen 1 can be measured or imaged over a wide range.

In a case where the oscillator array 201 is relatively moved by the actuator 202, it is desired that a liquid be filled between the oscillator array 201 and the fixing tool 211. In the case of the configuration in FIG. 1, the oscillator array 201 is disposed in the liquid 211b of the later-described fixing tool 211.

In the Embodiment 1, as shown in FIGS. 1 to 4, the fixing tool 211 is configured to contain a liquid 211b by an elastic membrane member 211a. The drive mechanism (fixing tool pressure adjustment unit) 212 inflates the membrane member 211a as shown in FIGS. 2 and 3 by increasing an amount of the liquid 211b contained in the membrane member 211a, so as to press the membrane member 211a against at least a part of the specimen 1, thereby retaining the specimen 1. As a specific example, a silicone rubber can be used as the membrane member 211a, and a liquid such as water or ethanol can be used as the liquid 211b. A gel may be used instead of the liquid 211b.

In the examples of FIGS. 1 to 4, the fixing tool 211 includes a housing 211c that is not disposed between the oscillator array 201 and the specimen 1, and a part of the membrane member 211a is supported by the housing 211c. An opening 261 for inserting the specimen 1 is provided in the housing 211c as shown in FIG. 5.

As shown in FIGS. 1 to 5, in the Embodiment 1, a guide member 251 is further included, into which a tip of the specimen 1 is inserted. By guiding the specimen 1 with the guide member 251, a shape of the specimen 1 can be supported in a shape suitable for accurate measurement. In the examples of FIGS. 1 to 5, since an imaged portion of the specimen 1 is a hand, the guide member 251 has a shape that guides a fingertip in a predetermined direction. In a case where the ultrasonic wave is also transmitted to and received from a portion (here, a fingertip) of the specimen 1 inserted into the guide member 251, it is desired that the guide member 251 is also formed of a material having an acoustic impedance equivalent to that of the specimen 1, similarly to the fixing tool 211. It is desired that the fixing tool 211 is formed of a material having an acoustic impedance with respect to the ultrasonic wave transmitted by the oscillator array 201 equivalent to that of the specimen 1. For example, in a case where the imaged portion of the specimen 1 is a hand, the fixing tool 211 is formed of a material having an acoustic impedance similar to that of a skin or fat. As a specific example, fluororesin is preferable.

In a case of using the guide member 251, it is desired that the fixing tool 211 retain a part of the specimen 1 that is not inserted into the guide member 251. For example, in a case where the specimen 1 is a hand and the guide member 251 guides a finger, the fixing tool 211 is configured to retain a palm of the hand. In the case of the hand, the palm of the hand is retained by the fixing tool 211, thereby effectively preventing a movement of the hand.

In a case of using the guide member 251, a gap is generated between the guide member 251 and the specimen 1, so that a liquid injection mechanism 221 that injects the liquid into the gap may be disposed. The liquid is desirably a material having an acoustic impedance with respect to the ultrasonic wave transmitted by the oscillator array 201 equivalent to that of the specimen 1, and for example, water or ethanol can be used.

The ultrasonic wave transmission and reception device of the Embodiment 1 further includes an image generation unit (control/calculation unit) 111 in addition to the above configurations. The control/calculation unit 111 generates an image of the specimen 1 by performing a predetermined calculation using a reception signal received by the oscillator 201.

The image generated by the control/calculation unit 111 may be any image. For example, the image may be an echo image used in an ultrasonic wave diagnostic device, a Doppler image for the purpose of obtaining a blood flow signal, or an image of a sound velocity or attenuation map obtained by an ultrasonic wave tomography method. Specifically, for example, the device of this embodiment can accurately calculate the echo image and the Doppler image as ultrasonic wave images, and a user can grasp a synovial thickening characteristic of a joint synovium inflammation and an inflow of a blood flow signal into a synovial membrane by using these images, and can perform an early diagnosis of rheumatoid based thereon.

Hereinafter, the ultrasonic wave transmission and reception device of the Embodiment 1 will be described in more detail with reference to the drawings.

<Specific Configuration of Device>

In the ultrasonic wave transmission and reception device of the Embodiment 1 shown in FIGS. 1 to 6, the transmission and reception of the ultrasonic wave is performed by the oscillator array 201 arrayed with one or two or more ultrasonic wave oscillators. The ultrasonic wave oscillator is an element that converts an electric signal (transmission signal) into an ultrasonic wave so as to transmit the electric signal, and then converts the received ultrasonic wave into an electric signal (reception signal).

The oscillator array 201 is connected to the control/calculation unit 111 that performs various electronic controls such as generation of the transmission signal, and performs a calculation of generating an image from the reception signal.

The control/calculation unit 111 is further connected to a UI 112 that inputs a certain instruction and information from a specimen or an examiner of the ultrasonic wave transmission and reception device, and to a display unit 113 that displays a current device state, an operation instruction to the specimen and a measurement result and the like, and these units can exchange information with each other.

<Control/Calculation Unit 111>

The control/calculation unit 111 includes a processor (for example, a CPU (Central Processing Unit) and a GPU (Graphics Processing Unit)), a memory in which a program is stored in advance, and an interface that transmits and receives the electrical signal. When the processor reads and executes the program, the transmission and reception of the ultrasonic wave to and from the oscillator array 201 through the interface, transmission of image data to the display unit 113, instruction exchange with the UI 112, and controls of the oscillator array actuator 202, the fixing unit pressure adjustment unit 212, and the liquid injection mechanism 221 and the like can be implemented by software. Further, an ultrasonic wave image 301 can be generated based on the ultrasonic wave reception signal, a result thereof can be displayed on the display unit 113, and an operation can be performed to change the above process.

A part of or the entire of the control/calculation unit 111 may be implemented by hardware. For example, the control/calculation unit 111 is configured using a custom IC such as an ASIC (Application Specific Integrated Circuit) or a programmable IC such as an FPGA (Field-Programmable Gate Array). By designing a circuit to implement the operation thereof, the control/calculation unit 111 can be implemented by the hardware.

<Oscillator Array 201>

In this embodiment, the ultrasonic wave transmission and reception device 101 is intended to perform an ultrasonic wave measurement of an entire imaging target region, that is, any position from a wrist to the fingertip of the specimen 1. Therefore, the oscillator array 201 includes a mechanism that transmits the ultrasonic wave to the entire imaging target region of the specimen 1 and receives the ultrasonic wave from the entire imaging target region.

In the ultrasonic wave transmission and reception device 101 shown in FIGS. 1 to 4, the oscillator array 201 is in an annular-ring shape as shown in FIG. 6A, and has a shape of two-dimensionally surrounding the specimen 1. Generally, since a bone has large ultrasonic wave attenuation, and signal intensity from a portion positioned on a back side of the bone is extremely weak against a transmission/reception source of the ultrasonic wave, the ultrasonic wave image 301 deteriorates. However, the above-described oscillator array 201 has the shape of two-dimensionally surrounding the specimen 1, so that a high-quality ultrasonic wave image can be obtained for an entire periphery of the bone.

Further, an ultrasonic wave signal passing through the specimen 1 can be obtained by providing a function of performing transmission and reception with the ultrasonic wave oscillators at opposing positions as shown in FIG. 6A. Accordingly, based on an arrival time, signal intensity and a signal waveform of the passing ultrasonic wave signal, the control/calculation unit 111 performs the calculation using the ultrasonic wave tomography method, and thereby the sound velocity, the attenuation and the like of the specimen 1 can be obtained.

Further, the oscillator array actuator 202 that mechanically moves the oscillator array 201 from the wrist of the specimen 1 along a fingertip direction is connected to the oscillator array 201. With such a configuration, the entire specimen 1 can be imaged.

<Modifications of Oscillator Array 201 and Actuator 202>

Modifications of the oscillator array 201 and the actuator 202 are shown in FIGS. 6B to 6E. As shown in FIG. 6B, the oscillator array actuator 202 may include a mechanism that changes a tilt angle of the oscillator array 201 and a drive mechanism that moves the oscillator array 201 in an in-plane direction, in addition to the movement in a direction from the wrist to the fingertip as shown in FIG. 6A (vertical movement in FIG. 6A).

As shown in FIG. 6C, the oscillator array 201 may have a two-dimensional annular-ring structure (cylindrical structure) in which an annular-ring shape is stacked in a center axis direction of the annular ring.

As shown in FIG. 6D, the oscillator array 201 may have the oscillators arrayed in a three-dimensional array as a bowl shape, for example.

As shown in FIG. 6E, the oscillator array 201 is in semi-annular-ring shape with a part of the annular ring missing, and may be configured to be capable of transmitting and receiving the ultrasonic wave to and from an entire region of the specimen by the actuator 202. With such a configuration, the ultrasonic wave can be transmitted to and received from substantially an entire periphery of a portion serving as a measurement target of the specimen 1, and the same effect as in the configuration shown in FIG. 6A can be obtained.

Although the oscillator array 201 has an annular-ring shape or a combination or a part thereof in FIGS. 6A to 6E, the oscillator array 201 may have any other shapes, for example, an elliptical shape. Alternatively, as shown in FIG. 6F, the oscillator array 201 may include two linear oscillator arrays in which oscillators are linearly arrayed. A manufacturing cost of the oscillator array can be reduced by using the linear oscillator arrays.

<Fixing Tool 211>

In the Embodiment 1, the fixing tool 211 fixes the specimen 1 by pressing the same from both a palm side and a back side of the specimen 1. Besides the press-fixing method shown in the Embodiment 1, for example, a suction-fixing method may be adopted as a fixing method.

In the Embodiment 1, as described above, the fixing tool 211 includes the membrane member 211a having a bag shape and elasticity, and the liquid 211b is contained in the membrane member 211a. The fixing tool pressure adjustment unit 212 can change a pressure applied to the specimen 1 by adjusting a pressure inside the fixing tool 211. For example, the fixing tool pressure adjustment unit 212 may be a structure that adjusts the pressure by adjusting an amount of the liquid 211b contained in the membrane member 211a, or a structure that adjusts the pressure by inserting a member changing a volume of the membrane member 211a. Specifically, a piston can be used as the fixing tool pressure adjustment unit 212. Further, the fixing tool 211 includes a pressure sensor 213 therein, a pressure inside the liquid 211b can be measured by the pressure sensor 213, and thereby the pressure applied to the specimen 1 can be detected.

A medium with good acoustic propagation characteristics is used for the membrane member 211a and the liquid 211b inside the same. In this embodiment, the medium having good acoustic propagation characteristics means a medium having a small ultrasonic wave attenuation coefficient and, as described above, having an acoustic impedance and a sound velocity close to those of the specimen represented by a human skin and fat. The attenuation coefficient is desirably 10 dB or less at a frequency of an ultrasonic wave to be transmitted and received.

The ultrasonic wave attenuation in a propagation medium can be prevented by using a medium having good acoustic propagation characteristics as the membrane member 211a and the liquid 211b that are positioned at a propagation path of the ultrasonic wave transmitted to and received from the oscillator array 201. Moreover, reflection at an interface between different media can be prevented. Thus, an ultrasonic wave signal scattered in the specimen can be detected with high efficiency. As a result, image quality of the ultrasonic wave image 301 can be improved.

Further, the medium having a sound velocity close to that of the specimen 1 is used as the membrane member 211a and the liquid 211b, thereby an influence of refraction at an interface between media of the ultrasonic wave is reduced, and particularly, in generation of the ultrasonic wave image 301 that performs a calculation assuming linear propagation, the quality of the ultrasonic wave image 301 can be improved.

For example, silicone can be used as a material of the membrane member 211a, and water can be preferably used as the liquid 211b inside the fixing tool 211.

The pressure adjustment performed by the fixing tool pressure adjustment unit 212 may be manually controlled by the specimen 1 himself/herself, an examination technician and the like, and may be automatically controlled by the control/calculation unit 111.

In a case where the fixing tool pressure adjustment unit 212 is controlled by the control/calculation unit 111, the UI 112 may enable the specimen, the examination technician and the like to set the pressure, or control the pressure to be a predetermined pressure. The pressure adjustment may be performed by adjusting the amount of the liquid 211b, or feedback control for the fixing tool pressure adjustment unit 212 may be performed such that a measurement result of the pressure sensor 213 becomes a set pressure.

Accordingly, the ultrasonic wave image 301 can be generated with high accuracy by preventing the movement of the specimen 1 in the ultrasonic wave measurement (later-described step S108) by the fixing tool 211. Moreover, since both attenuation amounts of the ultrasonic wave and the ultrasonic wave refraction are small at a propagation path other than the specimen 1, a high-quality ultrasonic wave image can be generated.

A positional relationship between the oscillator array 201 and the fixing tool 211 is as shown in FIG. 1, and the oscillator array 201 may be present inside a bag of the fixing tool 211 and co-exist with the liquid 211b, and the oscillator array 201 may be positioned outside the fixing tool 211 and in contact with the fixing tool 211 through the medium having good acoustic propagation characteristics (for example, a gel).

<Wrist Fixing Tool 231>

In the ultrasonic wave transmission and reception device of the Embodiment 1, as shown in FIGS. 1 to 3, a second fixing tool (wrist fixing tool) 231 that fixes the specimen is provided further outside the fixing tool 211. The wrist fixing tool 231 is provided around the opening 261 through which the specimen (hand) 1 of the housing 211c is inserted. The wrist fixing tool 231 fixes the wrist of the specimen 1. The wrist fixing tool 231 is positioned at a location where the ultrasonic wave is not propagated, and has no limitation on acoustic propagation characteristics relating to a material and a structure to be used.

The wrist fixing tool may be fixed by fastening with a band-shaped fastener, or may be fixed by press, or may be fixed by suction.

Further, the wrist fixing tool 231 may enable the specimen, the examination technician and the like to fix the wrist manually, or may enable the control/calculation unit 111 to adjust fixing, releasing, a fixing pressure and the like.

The wrist is fixed by the wrist fixing tool 231, so that during the ultrasonic wave measurement (later-described step S108), the movement of the specimen 1 can be further prevented and an ultrasonic wave image with less blur can be generated.

<Guide Member (Fingertip Guide) 251>

FIG. 2 shows a cross-sectional view of the ultrasonic wave transmission and reception device 101 at an angle rotated by 90 degrees from FIG. 1. The guide member (hereinafter, referred to as a fingertip guide) 251 serves to guide the finger such that the finger of the specimen 1 naturally spreads.

The fingertip guide 251 is formed of a material that has the good acoustic propagation characteristics as described above and that keeps a shape even hit by a finger or the like. For example, fluororesin is used. When a finger is in contact with an adjacent finger, transmission and reception signals of the ultrasonic wave to and from a contacting surface are greatly attenuated by the finger and a bone inside, and the intensity of the ultrasonic wave propagating to a side surface of the adjacent finger is greatly attenuated. Therefore, it is difficult to obtain a sufficient ultrasonic wave scattering signal to generate the ultrasonic wave image 301, but the fingers can be naturally guided by the fingertip guide 251 so as be separated from each other. Further, since the fingertip guide 251 is formed of the medium having good acoustic propagation characteristics, the ultrasonic wave attenuation can be reduced inside the fingertip guide and at a boundary surface of the fingertip guide. Therefore, transmission and reception of an ultrasonic wave through the side surface of the finger can be performed with high signal intensity, and sufficient signal intensity of the ultrasonic wave can be obtained to generate the ultrasonic wave image 301.

<Liquid Injection Mechanism 221>

The liquid injection mechanism 221 injects an acoustic matching liquid 222 between the specimen 1 and the fingertip guide 251, and between the specimen 1 and the fixing tool 211 (the membrane member 211a). The liquid injection mechanism 221 includes an injection tank 221a that stores the acoustic matching liquid 222 to be injected, a waste liquid tank 221b that stores a waste liquid 223, an injection pipe 221c, a waste liquid pipe 221d, and valves 221e provided at the injection pipe 221c and the waste liquid pipe 221d. The acoustic matching liquid 222 in the injection tank 222a is injected between the specimen 1 and the fingertip guide 251 and between the specimen 1 and the fixing tool 211 (the membrane member 211a), through the injection pipe 221c, by controlling the valve 221e by the control/calculation unit 111. Further, after the measurement is completed, the control/calculation unit 111 controls the valve 221e, so as to recover the acoustic matching liquid 222 between the specimen 1 and the fingertip guide 251 and between the specimen 1 and the fixing tool 211 (the membrane member 211a) as the waste liquid 223 after use, through the waste liquid pipe 221d, to the waste liquid tank 221b.

A liquid injection port of the injection pipe 221c is disposed, for example, at a lower portion of the fingertip guide 251 or near the opening 261 on an upper portion of the fixing tool 211. Accordingly, when the injection port of the liquid injection mechanism 211 is disposed at a position that is not the propagation path of the ultrasonic wave, the liquid injection mechanism 221 does not hinder the transmission and reception of the ultrasonic wave. Therefore, deterioration of the ultrasonic wave image 301 due to the presence of the liquid injection mechanism 221 can be prevented.

Here, the acoustic matching liquid 222 is a liquid having good acoustic propagation characteristics (a liquid having acoustic impedance and sound velocity similar to those of the specimen 1), and, for example, is preferably water or ethanol.

The acoustic matching liquid 222 reduces reflection of the ultrasonic wave caused by a space remaining between the specimen 1 and the fingertip guide 251 and between the specimen 1 and the fixing tool 211, improves propagation of the ultrasonic wave between the oscillator array 201 and the specimen 1, and enables the generated ultrasonic wave image 301 to have a high quality.

Further, the liquid injection mechanism 221 may include a liquid suction mechanism so as to recover the acoustic matching liquid (waste liquid) more efficiently. The examination time can be shortened by including the suction mechanism.

The tanks 221a and 221b that store the acoustic matching liquid 222 and the acoustic matching liquid (waste liquid) 223 are not limited to a tank configuration, and may be configured to be capable of performing replenishment/replacement/disposal operations.

<Dryer 241>

The ultrasonic wave transmission and reception device of this embodiment includes a dryer 241 on an upper portion of the wrist fixing tool 231 as shown in FIGS. 1 to 3. The dryer 241 dries the acoustic matching liquid 222 remaining in the specimen 1 after the imaging is completed. For example, a structure that blows warm air to the specimen 1 so as to blow away and dry the acoustic matching liquid adhering to the specimen 1 can be used as the dryer 241. Accordingly, the acoustic matching liquid 222 adhering to the specimen 1 does not need to be wiped off by the specimen after the examination is completed, and the examination can be completed comfortably.

<Operation of Each Unit of Device>

Here, with reference to FIGS. 7 and 8, an ultrasonic wave imaging operation performed by the ultrasonic wave transmission and reception device 101 will be described below. A flow of FIG. 7 is a flowchart illustrating an ultrasonic wave imaging sequence executed under the control of the control/calculation unit 111 in the Embodiment 1. Further, FIG. 8 shows information exchange between components.

[Steps S101, S102]

In a case where a power source of the ultrasonic wave transmission and reception device is turned on and an activation instruction of the device is received from the specimen or the technician via the UI 112 (step S101), the control/calculation unit 111 enables the display unit 113 to display an instruction of inserting a hand of the specimen 1 through the hand insertion opening 261 (step S102). The specimen 1 follows the displayed instruction, and inserts each finger thereof into the fingertip guide 251 through the hand insertion opening 261.

[Steps S103, S104]

When receiving an instruction of fixing the specimen 1 from the specimen or the technician via the UI 112 (step S103), the control/calculation unit 111 controls the fixing tool pressure adjustment unit 212 to increase the pressure inside the fixing tool 211 and press the membrane member 211a against the specimen 1 so as to press and fix the same (step S104).

In adding to receiving the instruction of fixing the specimen 1 by the control/calculation unit 111 via the UI 112, a sensor that senses the presence of the specimen 1 is disposed inside the ultrasonic wave transmission and reception device 101. In a case where the sensor senses the presence of the specimen 1, the control/calculation unit 111 may be replaced with a configuration that instructs the fixing tool pressure adjustment unit 212 to fix the specimen 1.

The oscillator array 201 may be used as the sensor. For example, in a case where the oscillator array 201 transmits and receives the ultrasonic wave and senses the presence of the specimen 1 based on the reception signal of the ultrasonic wave, the control/calculation unit 111 can have a configuration that instructs the fixing tool pressure adjustment unit 212 to fix the specimen 1.

[Step S105]

When the pressure applied to the specimen 1 by the fixing tool 211 sufficiently rises, a signal indicating completion of specimen fixation is output from the fixing tool pressure adjustment unit 212 to the control/calculation unit 111 (step S105). For example, in a case where the pressure applied to the specimen 1 is measured by the pressure sensor 213 and exceeds a predetermined pressure value, the fixing tool pressure adjustment unit 212 may stop the pressure rise and output an instruction of completion of the specimen fixation to the control/calculation unit 111. If the specimen 1 determines that the pressure sufficiently rises according to subjectivity of the specimen 1, the specimen 1 may input that the pressure sufficiently rises by operating the UI 112 by himself/herself. In response to this, the fixing tool pressure adjustment unit 212 may be configured to stop the pressure rise and output the instruction of the completion of the specimen fixation to the control/calculation unit 111.

[Steps S106, S107]

When receiving the instruction of the completion of the specimen fixation (step S105), the control/calculation unit 111 instructs the liquid injection mechanism 221 to inject the acoustic matching liquid 222 between the specimen 1 and the fingertip guide 251 and between the specimen 1 and the fixing tool 211 (step S106). After a sufficient amount of the acoustic matching liquid 222 is injected, the liquid injection mechanism 221 outputs a signal indicating completion of the acoustic matching liquid injection to the control/calculation unit 111 (step S107).

Whether a sufficient amount of the acoustic matching liquid 222 has been injected can be determined by the liquid injection mechanism 221 determining whether a liquid level height has reached a predetermined height, in which the liquid level height of the acoustic matching liquid 222 injected between the fixing tool 211 and the specimen or the liquid level height of the acoustic matching liquid 222 in the injection tank 221a is measured by a liquid surface sensor (not shown) disposed in the fixing tool 211 or the injection tank 221a. In addition, whether a sufficient amount of the acoustic matching liquid 222 has been injected between the fixing tool 211 and the specimen 1 may be determined by the specimen 1 subjectively (visual or the like). In a case where the specimen 1 determines that a sufficient amount has been injected, the specimen 1 inputs that a sufficient amount of the acoustic matching liquid 222 has been injected by operating the UI 112 by himself/herself. In a case where a sufficient amount of the acoustic matching liquid 222 has been injected, the liquid injection mechanism 221 stops the injection and outputs a signal indicating the completion of the acoustic matching liquid injection to the control/calculation unit 111.

[Step S108]

When receiving a signal of the completion of the acoustic matching liquid injection (step S107), the control/calculation unit 111 starts the ultrasonic wave measurement (step S108).

With reference to the FIGS. 9 and 10, the information exchange in the ultrasonic wave measurement (step S108) will be described in detail.

FIG. 9 is a detailed flowchart of step S108 in FIG. 7, and FIG. 10 is a diagram showing the detailed information exchange of step S108.

The control/calculation unit 111 first transmits and receives an ultrasonic wave (step S201). Specifically, an electrical ultrasonic wave transmission signal is transmitted to the oscillator array 201. The oscillator array 201 converts the electrical signal into an ultrasonic wave and transmits the ultrasonic wave to the specimen 1. Subsequently, the ultrasonic wave scattering in, reflected from, or passing through the specimen 1 is received by the oscillator array 201. The oscillator array 201 converts the ultrasonic wave signal into an electrical signal and transmits the electrical ultrasonic wave reception signal to the control/calculation unit 111. The control/calculation unit 111 stores the received ultrasonic wave reception signal in a memory.

Next, in order to obtain an entire image of the specimen 1 (for example, a hand), the control/calculation unit 111 mechanically drives the oscillator array 201 by the oscillator array actuator 202 (steps S202, S205). Specifically, the control/calculation unit 111 determines whether the number of mechanical driving steps of the oscillator array 201 has reached a predetermined number (step S202), and if not, the process proceeds to step S205, and the control/calculation unit 111 transmits an instruction of mechanically driving (moving) the oscillator array 201 to the oscillator array actuator 202 (step S205). When receiving the drive instruction from the control/calculation unit 111, the oscillator array actuator 202 drives the oscillator array 201 by one step. Then, the control/calculation unit 111 returns to step S201, and transmits and receives an ultrasonic wave again. This process is repeated until the number of driving steps reaches the predetermined number (step S202). If the number of the driving steps reaches the predetermined number in step S202, the control/calculation unit 111 determines that scan (array scan) over a predetermined range by the oscillator array 201 has been completed (step S202), and the process proceeds to step S203.

The control/calculation unit 111 generates the ultrasonic wave image 301 from the reception signal obtained in step S201 (step S203), and enables the display unit 112 to display an image result thereof (step S204).

Steps S203 and S204 may be performed at any time after each step S201, and may be performed between step S205 and step S201, for example, for each scan step (driving step).
[Step S109]

The control/calculation unit 111 determines whether the ultrasonic wave measurement (step S108) has been completed by the above steps S201 to S205 (step S109). The control/calculation unit 111 may determine that the ultrasonic wave measurement has been completed in a case where a predetermined ultrasonic wave imaging sequence (steps S201 to S205) has been completed successfully, may determine whether image taking data can be obtained as assumed based on the generated ultrasonic wave image 301, and may determine that the ultrasonic wave measurement has been completed in a case where the imaging can be completed as assumed. Further, in a case where the control/calculation unit 111 enables the display unit 113 to display the generated ultrasonic wave image thereon, and the specimen 1 or the examination technician who has seen such an ultrasonic wave image determines that the imaging is good, and makes an input indicating that the ultrasonic wave measurement has been completed via the UI 112, the control/calculation unit 111 may determine that the ultrasonic wave measurement has been completed.
[Step S110]

When determining that the ultrasonic wave measurement has been completed (step S109), the control/calculation unit 111 instructs the fixing tool pressure adjustment unit 212 to reduce the pressure of the fixing tool 211 (step S110). Accordingly, when the fixing tool pressure adjustment unit 212 reduces the pressure applied to the specimen 1 by the fixing tool 211, the specimen (hand) 1 can be pulled out of the ultrasonic wave transmission and reception device 101.

When the pressure reduction of the fixing tool 211 is completed, the fixing tool pressure adjustment unit 212 outputs a signal indicating completion of the fixing tool pressure reduction to the control/calculation unit 111. For example, in a case where the pressure sensor 213 indicates a pressure equal to or less than a predetermined pressure, or in a case where the fixing tool pressure adjustment unit 212 extracts a predetermined amount of water from the fixing tool 211, the fixing tool pressure adjustment unit 213 determines that the pressure reduction of the fixing tool is completed. Further, the specimen may input that the pressure reduction of the fixing tool has been completed via the UI 112.
[Step S111]

Next, the control/calculation unit 111 instructs the liquid injection mechanism 221 to discharge the acoustic matching liquid 222 (step S111). The liquid injection mechanism 221 operates the valve 221 so as to recover the acoustic matching liquid 222 between the specimen 1 and the fingertip guide 251 and between the specimen 1 and the fixing tool 211 (membrane member 211a) through the waste liquid pipe 221d to the waste liquid tank 221b.

After step S111, the dryer 241 may be operated to dry the acoustic matching liquid 222 remaining in the specimen 1 when the specimen 1 is pulled out of the ultrasonic wave transmission and reception device 101. Comfort and hygiene of the examination are improved by drying the specimen 1.
[Step S112]

Next, in a case of receiving an instruction of terminating the device from the specimen 1 or the technician (step S112), the control/calculation unit 111 completes the operation of the ultrasonic wave transmission and reception device 101. In a case where there is no termination instruction, the process returns to step S102, and the above steps S102 to S111 are repeated again.

The ultrasonic wave transmission and reception device operating as in the above flow in FIG. 7 can perform the imaging sequence of retaining the specimen 1 and then transmitting and receiving the ultrasonic wave while automatically controlling each unit, and can automatically image a highly accurate ultrasonic wave image while preventing the movement of the specimen 1. Therefore, the examination can be performed independent of the skill of an ultrasonic wave examiner (technician). The examination can also be performed by the specimen 1 himself/herself. Further, since the measurement can be repeated by the same measurement method, a temporal change of the specimen 1 can be easily monitored. Therefore, rheumatism diagnosis such as a change of an ultrasonic wave pathological condition and a determination of a therapeutic effect can be performed with higher accuracy, based on the highly accurate ultrasonic wave image.

In the Embodiment 1, an example in which the specimen 1 is a portion from the fingertip to the wrist has been described, but the specimen 1 may be other portions. Other examples include a portion from ankles to toes, limbs including knee/elbow joints, abdomen and breast. As in the examination thereof, the fingertip guide 251, the fixing tool 211 and the hand insertion opening 261 may have an appropriate shape corresponding to the shape of each portion, and the oscillator array 201 may have an appropriate size according to a size of each measurement portion, so that the imaging can be performed with the same effect as described in this embodiment.
Modification 1 of Embodiment 1

FIG. 11 shows a Modification 1 of the Embodiment 1. A direction where the specimen 1 is inserted into the ultrasonic wave transmission and reception device 101 of the Embodiment 1 is a vertical direction, but is oriented in a horizontal direction in the Modification 1. In a configuration of the Modification 1, since the palm of the specimen 1 faces a gravity direction, that is, downward, the specimen (hand) 1 is more stable in the ultrasonic wave transmission and reception device 101 and the movement of the specimen 1 is reduced during the measurement.

Accordingly, the pressure applied to the specimen 1 by the fixing tool 211 that fixes the specimen 1 can be reduced compared with the Embodiment 1, and the manufacturing cost of the device can be reduced; meanwhile, the comfort of the specimen 1 can be improved.

The direction of the ultrasonic wave transmission and reception device 101 is not limited thereto, and may be an oblique direction between the vertical direction shown in FIG. 1 and the horizontal direction shown in FIG. 11. An appropriate angle is selected in consideration of a size and a structure of the ultrasonic wave transmission and reception device, so that the palm of the specimen 1 can be oriented in a direction close to the gravity direction (downward) while preventing the acoustic matching liquid 222 from flowing out of the hand insertion opening 261. Therefore, the specimen 1 can be stabilized.

Other configurations of the Modification 1 are the same as those of the Embodiment 1, so the description thereof is omitted.

Modification 2 of Embodiment 1

FIG. 12 shows a Modification 2 of the Embodiment 1. In the Modification 2 of FIG. 12, a glove 271 having good acoustic propagation characteristics is attached to the specimen 1 in advance and then inserted into the opening 261 of the ultrasonic wave transmission and reception device 101. Since the glove 271 is used, the ultrasonic wave measurement is less likely to be influenced by a surface condition of the specimen 1, and a more reproducible and uniform examination can be provided.

Further, since the glove 271 can be thrown away and can be easily cleaned and sterilized in every use, the ultrasonic wave transmission and reception device 101 can be kept cleaner by attaching the glove 271 to the specimen 1, and a risk of hygiene such as virus infection can be reduced.

Rubber materials such as latex can be used as the glove 271. Since an elastic rubber material is used, adhesiveness between the specimen 1 and the glove 271 is improved, and a factor that inhibits ultrasonic wave propagation such as air between the specimen 1 and the glove can be reduced. Thus, a high-quality ultrasonic wave image 301 can be provided.

An acoustic matching agent 272 may be injected or applied between the glove 271 and the specimen 1. A medium having an acoustic impedance equivalent to that of the specimen 1, for example, a liquid such as water or ethanol, or a fluid such as a gel is used as the acoustic matching agent 272. Accordingly, a space between the glove 271 and the specimen 1 can be filled without a gap, and a high-quality ultrasonic wave image 301 can be provided.

Other configurations of the Modification 2 are the same as those of the embodiment 1, so the description thereof is omitted.

Embodiment 2

The ultrasonic wave transmission and reception device 101 of an Embodiment 2 will be described with reference to FIG. 13.

The ultrasonic wave transmission and reception device of the Embodiment 2 is different from that of the Embodiment 1 in a structure of the fixing tool 211 for retaining the specimen 1, and a drive mechanism 212 that presses at least a part of the fixing tool 211 against the specimen 1 so as to retain the specimen 1.

As shown in FIG. 13, the fixing tool 211 includes a member 130a having a predetermined shape, and the drive mechanism 131 is a mechanism that applies a force to move the member 130a in a direction where the member 130a is pressed against the specimen 1. Specifically, the member 130a is formed of an elastic body, and an elastic material is formed of a material having good ultrasonic wave acoustic propagation characteristics (an acoustic impedance and a sound velocity are equivalent to those of the specimen 1 and an ultrasonic wave attenuation coefficient is sufficiently small), such as a silicone rubber. A spring or an actuator can be used as the drive mechanism 131.

The member 130a is provided with a space in which the oscillator array 201 is disposed and the oscillator array 201 can be scanned, and the oscillator array 201 and the actuator 202 are disposed in the space. The space is filled with a liquid having an acoustic impedance and a sound velocity equivalent to those of the specimen 1 and a sufficiently small ultrasonic wave attenuation coefficient. The space, for example, is doughnut-shaped.

Even in a case where the member 130a is moved by the drive mechanism 131 from an open state where the specimen 1 is not pressed to a state where the specimen 1 is pressed and retained, a space size that the member 130a is not in contact with the oscillator array 120 is ensured. With such a structure, although the member 130a of the fixing tool 211 is moved so as to move the specimen 1 for retaining, the position of the oscillator array 201 can be kept unchanged. Therefore, since an interval between the opposing oscillators can be kept, the same calculation as in the Embodiment 1 can be performed even in a case where a calculation such as image reconstruction is performed by the control/calculation unit 111 from the reception signal.

Other configurations of the Embodiment 2 are the same as those of the Embodiment 1, so the description thereof is omitted.

<Modification 1 of Embodiment 2>

FIG. 14 shows an ultrasonic wave transmission and reception device of a Modification 1 of the Embodiment 2. The ultrasonic wave transmission and reception device of FIG. 14 is configured in the same manner as in the Embodiment 2, in which the fixing tool 211 is the member 130a formed of an elastic body and is pressed against the specimen 1 by the actuator 131 so as to press the specimen 1 and retain specimen 1, but is different from that of the Embodiment 2 in that the oscillator array 201 is disposed outside the fixing tool 211. Since the oscillator array 201 is disposed in a space outside the fixing tool 211, the liquid 130b is filled in a space between the fixing tool 211 and the housing 211c outside the fixing tool 211.

The same effect as in the Embodiment 2 can be obtained in this modification.

Other configurations of the Modification 1 are the same as those of the Embodiment 2, so the description thereof is omitted.

Modification 2 of Embodiment 2

An ultrasonic wave transmission and reception device of a Modification 2 of the Embodiment 2 will be described with reference to FIG. 15.

The ultrasonic wave transmission and reception device of the Modification 2 is configured in the same manner as in the Embodiment 2, in which the fixing tool 211 is the member 130a formed of an elastic body and is pressed against the specimen 1 by the actuator 131 so as to press the specimen 1 and retain the specimen 1, but is different from that of the Embodiment 2 in that the oscillator array 201 is imbedded in the member 130a.

Further, the oscillator array 201 has a shape that is also different from that of the Embodiment 1, having a structure in which the ultrasonic wave oscillators are not only arranged in a circumferential direction but also in a scan direction of (vertical direction) the oscillator array 201 of the Embodiment 2 such that the ultrasonic wave transmission and reception can be performed in a predetermined range of the specimen 1 even if the oscillator array 201 is not scanned (moved), for example, having a cylindrical structure.

Accordingly, the vertical scan (movement) of the oscillator array 201 is not necessary, so that the actuator 202 is not provided in the Modification 2. Further, since the oscillator array 201 is not moved, the oscillator array 201 and the member 130a adhere to each other with no gap therebetween.

In the Modification 2, since the oscillator array 201 is not only arrayed in the circumferential direction but also in the vertical direction, the entire specimen 1 can be imaged even if the oscillator array 201 cannot be moved in the vertical direction.

Further, in the structure of the Modification 2, the position of the oscillator array 201 changes as the member 130a of the fixing tool 211 moves. That is, an interval between opposing oscillators or adjacent oscillators changes according to a thickness of the specimen 1. Thus, when a calculation such as image reconstruction is performed by the control/calculation unit 111 from the reception signal, a positional relationship of the oscillators is obtained from a driving amount of the actuator 131, and a distance between the oscillators in an equation used for the calculation of the image generation is corrected. Accordingly, the ultrasonic wave image can be generated with high accuracy even if the positional relationship of the oscillators changes.

Other configurations of the Modification 2 are the same as those of the Embodiment 2, so the description thereof is omitted.

Modification 3 of Embodiment 2

An ultrasonic wave transmission and reception device of a Modification 3 of the Embodiment 2 will be described with reference to FIG. 16.

FIG. 16 is a cross-sectional view of the ultrasonic wave transmission and reception device of the Modification 3 shown in the horizontal direction. The fixing tool 211 of the Modification 3 is an annular-ring-shaped elastic body (for example, silicone rubber) 130a of which a part is cut out. The actuator 131 has a structure of being disposed at the cut-out position of the annular-ring-shaped elastic body of the fixing tool 211, and pressing and fixing the specimen 1 by applying a force in a direction where the annular-ring-shaped elastic body is tightened.

The liquid (for example, water) 130b is filled between the oscillator array 201 and the fixing tool 211. However, the structure of the oscillator array 201 is not limited to an annular ring shape, and the oscillator arrays shown in FIGS. 6A to 6F and the like may also be used.

Other configurations of the Modification 3 are the same as those of the Embodiment 2, so the description thereof is omitted.

In the above Embodiment 2 and Modifications 1 to 3 thereof, a wide range of the specimen 1 can be sandwiched by the fixing tool 111 (member 130a), so that the injection of the acoustic matching liquid 222 between the fixing tool 211 and the specimen 1 may be omitted. FIG. 17 shows an operation flow of the ultrasonic wave transmission and reception device in this case. As shown in FIG. 17, the steps S106 and S107 the flow in FIG. 7 are omitted to omit the injection of the acoustic matching liquid 222 between the fixing tool 211 and the specimen 1, so that the ultrasonic wave measurement can be performed in a simplified manner.

REFERENCE SIGN LIST 1 specimen
101 ultrasonic wave transmission and reception device
111 control/calculation unit
112 UI
113 display unit
201 oscillator array
202 oscillator array actuator
211 fixing tool
212 fixing tool pressure adjustment unit
213 pressure sensor
211b liquid
221 liquid injection mechanism
222 acoustic matching liquid
223 acoustic matching liquid (waste liquid)
221e valve
231 wrist fixing tool
241 dryer
251 fingertip guide
261 hand insertion opening
271 glove
272 acoustic matching agent inside glove
301 ultrasonic wave image

The invention claimed is:

1. An ultrasonic wave transmission and reception device, comprising:
an oscillator array that is arrayed with an oscillator, the oscillator transmitting and receiving an ultrasonic wave;
a fixing tool that is disposed between the oscillator array and a specimen and retains the specimen;
a drive mechanism that presses at least a part of the fixing tool against the specimen so as to retain the specimen;
a guide member into which a tip of the specimen is inserted; and
a liquid injection mechanism that injects the liquid between the guide member and the specimen such that the liquid and the tip inside the guide member are in contact,
wherein an ultrasonic wave transmitted by the oscillator array passes through the fixing tool and irradiates on the specimen, the oscillator array and the fixing tool are disposed in a positional relationship such that the ultrasonic wave reflected by and/or passing through the specimen and passing through the fixing tool is received, and
wherein the fixing tool retains a part of the specimen that is not inserted into the guide member.

2. The ultrasonic wave transmission and reception device according to claim 1, wherein the fixing tool is formed of a material having an acoustic impedance with respect to the ultrasonic wave transmitted by the oscillator array equivalent to that of the specimen.

3. The ultrasonic wave transmission and reception device according to claim 1, wherein the oscillator array has a shape that two-dimensionally surrounds at least a part of a periphery of the specimen.

4. The ultrasonic wave transmission and reception device according to claim 1, wherein the oscillator array includes at least one pair of oscillators disposed at opposing positions with the specimen sandwiched therebetween.

5. The ultrasonic wave transmission and reception device according to claim 1, wherein the fixing tool includes an elastic membrane member and containing a liquid, and
the drive mechanism includes a fixing tool pressure adjustment unit that inflates the membrane member by increasing an amount of the liquid contained in the membrane member so as to press the membrane member against at least a part of the specimen, thereby retaining the specimen.

6. The ultrasonic wave transmission and reception device according to claim 1, wherein the fixing tool is a member having a predetermined shape, and
the drive mechanism includes a mechanism that applies a force to move the member in a direction where the member is pressed against the specimen.

7. The ultrasonic wave transmission and reception device according to claim 6, wherein the oscillator array is disposed in the member.

8. The ultrasonic wave transmission and reception device according to claim 7, further comprising an image generation unit that generates an image of the specimen by performing a predetermined calculation using a reception signal received by the oscillator,
  wherein after the member is moved by the drive mechanism in the direction where the member is pressed against the specimen, the image generation unit determines a distance between the oscillator and the specimen and uses the distance information to perform the calculation, thereby generating an image.

9. The ultrasonic wave transmission and reception device according to claim 1, further comprising an actuator that moves the oscillator array relative to the specimen.

10. The ultrasonic wave transmission and reception device according to claim 9, wherein the liquid is filled between the oscillator array and the fixing tool.

11. The ultrasonic wave transmission and reception device according to claim 1, wherein the specimen is a hand, and the guide member has a shape that guides a position of a finger of the hand.

12. The ultrasonic wave transmission and reception device according to claim 1, wherein the liquid injection mechanism injects and discharges the liquid between the fixing tool and the specimen.

13. The ultrasonic wave transmission and reception device according to claim 12, wherein the liquid discharged via the liquid injection mechanism is held in a separate container from the liquid injected.

14. The ultrasonic wave transmission and reception device according to claim 1, further comprising a second fixing tool that fixes the specimen further outside the fixing tool.

15. The ultrasonic wave transmission and reception device according to claim 1, further comprising a dryer.

16. The ultrasonic wave transmission and reception device according to claim 15, wherein on a condition that the liquid is discharged from between the fixing tool and the specimen, the dryer dries the specimen.

* * * * *